(12) United States Patent
Xin et al.

(10) Patent No.: US 11,494,903 B2
(45) Date of Patent: Nov. 8, 2022

(54) SYSTEMS AND METHODS FOR IMAGE DATA ACQUISITION

(71) Applicant: SHANGHAI UNITED IMAGING HEALTHCARE CO., LTD., Shanghai (CN)

(72) Inventors: Yang Xin, Shanghai (CN); Tingrong Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 204 days.

(21) Appl. No.: 16/898,419

(22) Filed: Jun. 10, 2020

(65) Prior Publication Data

US 2021/0133962 A1   May 6, 2021

(30) Foreign Application Priority Data

Nov. 1, 2019   (CN) .......................... 201911061103.8

(51) Int. Cl.
| | |
|---|---|
| *G06K 9/00* | (2022.01) |
| *G06T 7/00* | (2017.01) |
| *A61B 5/00* | (2006.01) |
| *A61B 5/055* | (2006.01) |
| *A61B 6/00* | (2006.01) |
| *A61B 6/03* | (2006.01) |
| *G01R 33/56* | (2006.01) |
| *G01R 33/54* | (2006.01) |

(52) U.S. Cl.
CPC .......... *G06T 7/0012* (2013.01); *A61B 5/0035* (2013.01); *A61B 5/055* (2013.01); *A61B 5/4566* (2013.01); *A61B 6/037* (2013.01); *A61B 6/505* (2013.01); *A61B 6/5247* (2013.01); *G01R 33/546* (2013.01); *G01R 33/5608* (2013.01); *A61B 5/7264* (2013.01); *G06T 2200/24* (2013.01); *G06T 2207/30012* (2013.01)

(58) Field of Classification Search
CPC .................................................... G06T 7/0012
See application file for complete search history.

(56) References Cited

U.S. PATENT DOCUMENTS

| | | | | |
|---|---|---|---|---|
| 9,940,545 | B2* | 4/2018 | Rezaee | G06V 10/446 |
| 2009/0105582 | A1* | 4/2009 | Dougherty | G01R 33/4824 |
| | | | | 600/420 |
| 2012/0215110 | A1* | 8/2012 | Wilkening | G01S 7/52095 |
| | | | | 600/453 |
| 2013/0060146 | A1* | 3/2013 | Yang | A61B 5/055 |
| | | | | 600/476 |

(Continued)

*Primary Examiner* — Oneal R Mistry
(74) *Attorney, Agent, or Firm* — Metis IP LLC

(57) ABSTRACT

The present disclosure provides a system and method for image data acquisition. The method may include obtaining image data of a subject including a first type of tissue and a second type of tissue. The method may include determining, based on the image data of the subject, a target portion including at least a portion of at least one of the first type of tissue or the second type of tissue. The method may include determining, based at least in part on the target portion represented in the image data, a scan mode corresponding to the target portion. The method may include causing an imaging device to acquire, based on the scan mode, image data of the target portion.

15 Claims, 19 Drawing Sheets

(56) References Cited

U.S. PATENT DOCUMENTS

| | | | | |
|---|---|---|---|---|
| 2014/0003684 | A1* | 1/2014 | Ayed | G06T 7/11 |
| | | | | 382/128 |
| 2020/0058098 | A1* | 2/2020 | Hirakawa | G06T 7/97 |
| 2020/0222025 | A1* | 7/2020 | Prater | A61B 8/4483 |
| 2020/0311456 | A1* | 10/2020 | Ji | G06V 10/82 |
| 2020/0320786 | A1* | 10/2020 | Kadoury | G06N 3/0454 |
| 2021/0216822 | A1* | 7/2021 | Paik | G06F 3/013 |

* cited by examiner

FIG. 12C

| 1 Protocol 1 | |
|---|---|
| 2 Protocol 2 | 1 |
| 3 Protocol 3 | 2 |
| 4 Protocol 4 | 2 |
| 5 Protocol 5 | 1 |
| 6 Protocol 6 | 5 |
| 7 Protocol 7 | ×5 |
| 8 Protocol 8 | |

FIG. 14B

Name

User-defined 2

☐ Direction of Slice Group
☐ Position of Slice Group
☐ Thickness of Slice
☐ Phase Coding Direction
☐ Slice Gap
☐ Coil
☐ TR
☐ TE

FIG. 15B

SYSTEMS AND METHODS FOR IMAGE DATA ACQUISITION

CROSS-REFERENCE TO RELATED APPLICATIONS

This application claims priority to Chinese Patent Application No. 201911061103.8, filed on Nov. 1, 2019, the contents of which are hereby incorporated by reference.

TECHNICAL FIELD

The disclosure generally relates to medical systems and methods, and more particularly relates to medical systems and methods for image data acquisition.

BACKGROUND

When a spinal lesion or injury occurs, an imaging scan may need to be performed on the position of the spinal lesion or injury. Before the beginning of the imaging scan for a spinal, an operator (e.g., a doctor) needs to determine a scan range of the spinal and determine a scan mode based on the scan range manually according to the clinical experience of the operator, which may often be time-consuming. And the scan range and scan mode manually determined by the operator may be of low accuracy, thereby decreasing the efficiency and accuracy of image data acquisition. Thus, it is desired to provide systems and methods for image data acquisition with improved accuracy and/or efficiency.

SUMMARY

According to a first aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain image data of a subject including a first type of tissue and a second type of tissue. The system may determine, based on the image data of the subject, a target portion including at least a portion of at least one of the first type of tissue or the second type of tissue. The system may determine, based at least in part on the target portion represented in the image data, a scan mode corresponding to the target portion. The system may cause an imaging device to acquire, based on the scan mode, image data of the target portion.

In some embodiments, the subject may include a spine. The first type of tissue may include one or more vertebrae. The second type of tissue may include one or more intervertebral discs.

In some embodiments, to determine, based on the image data of the subject, a target portion including at least a portion of at least one of the first type of tissue or the second type of tissue, the at least one processor may be configured to cause the system to perform the operations. The system may obtain an anatomical model. The system may further determine, based on the image data of the subject and the anatomical model, the target portion.

In some embodiments, to determine, based on the image data of the subject, a target portion including at least a portion of at least one of the first type of tissue or the second type of tissue, the at least one processor may be configured to cause the system to perform the operations. The system may determine, based on the image data of the subject, an anomaly result indicating whether an anomaly exists in at least one of the first type of tissue or the second type of tissue. The system may further determine, based on the anomaly result, the target portion.

In some embodiments, the anomaly result may include that the anomaly exists in the first type of tissue. The determining, based on the anomaly result, the target portion may include determining that the target portion includes the first type of tissue. The scan mode corresponding to the target portion may include a parallel scan with a plurality of groups of slices oriented at the same angle.

In some embodiments, the anomaly result may include that the anomaly exists in the second type of tissue. The determining, based on the anomaly result, the target portion may include determining that the target portion includes the second type of tissue. The scan mode corresponding to the target portion may include an interleaved scan with a plurality of groups of slices oriented at different angles.

In some embodiments, to cause an imaging device to acquire, based on the scan mode, image data of the target portion, the at least one processor may be further configured to cause the system to perform the operations. The system may obtain multiple scan protocols corresponding to the scan mode. The system may further synchronize, based on one or more links between the multiple scan protocols, parameters of one or more same types of the multiple scan protocols.

In some embodiments, the anomaly result may include that the anomaly exists in the first type of tissue and the second type of tissue. The determining, based on the anomaly result, the target portion may include determining, based on personalized data of the subject, the target portion including one of the first type of tissue and the second type of tissue.

In some embodiments, to cause an imaging device to acquire, based on the scan mode, image data of the target portion, the at least one processor may be further configured to cause the system to perform the operations. The system may perform a scanning of the target portion according to a first scan mode corresponding to the first type of tissue or a second scan mode corresponding to the first type of tissue. The system may further identify, based on the scanning, a change of the target portion between the first type of tissue and the second type of tissue. The system may further switch, in response to the identified change, the scan mode between the first scan mode and the second scan mode.

In some embodiments, to determine, based at least in part on the target portion represented in the image data, a scan mode corresponding to the target portion, the at least one processor may be further configured to cause the system to perform the operations. The system may determine, based at least in part on the target portion, one or more parameters of the scan mode. The one or more parameters of the scan mode may include at least one of one or more scan angles, a count of scan slices corresponding to each of the one or more scan angles, or a position of each of the scan slices.

In some embodiments, to cause the imaging device to acquire image data of the target portion, the at least one processor may be further configured to cause the system to perform the operations. The system may receive an input indicating an operation for adjusting the scan mode. In response to the received input, the system may further adjust the scan mode according to the input. The system may further cause an imaging device to acquire, based on the adjusted scan mode, image data of the target portion.

In some embodiments, the at least one processor may be further configured to cause the system to perform the operations. The system may receive an input indicating an operation for switching the scan mode. In response to the received input, the system may further switch the scan mode according to the input.

In some embodiments, the at least one processor may be further configured to cause the system to perform the operations. The system may receive an input indicating a change in the target portion. The system may further determine a switched scan mode corresponding to the changed target portion. The system may further cause the imaging device to acquire, based on the switched scan mode, image data of the changed target portion.

In some embodiments, to cause the imaging device to acquire image data of the target portion, the at least one processor may be further configured to cause the system to perform the operations. The system may receive an input indicating an operation for changing a scan range of the target portion. In response to the received input, the system may adjust the scan range. The system may further adjust the scan mode according to the adjusted scan range. The system may further cause the imaging device to acquire, based on the adjusted scan range and the adjusted scan mode, the image data of the target portion.

According to a second aspect of the present disclosure, a terminal device is provided. The terminal device may include at least one storage device storing executable instructions, and at least one processor in communication with a display screen. When executing the executable instructions, the at least one processor may cause the terminal device to perform one or more of the following operations. The terminal device may display, on the display screen, a user interface. The terminal device may detect, via the user interface, a user input relating to a scan mode. The terminal device may transmit, via the user interface, the user input to a processor, wherein the scan mode is provided by a process. The process may include obtaining image data of a subject including a first type of tissue and a second type of tissue. The process may further include determining, based on the image data of the subject, a target portion including at least a portion of at least one of the first type of tissue or the second type of tissue. The process may further include determining, based at least in part on the target portion represented in the image data, the scan mode corresponding to the target portion.

In some embodiments, the user input may include at least one of a confirmation of the scan mode, a rejection of the scan mode, a modification of the scan mode, or a selection of another scan mode from the plurality of scan modes.

In some embodiments, the user input may indicate an operation for changing the target portion corresponding to the scan mode. The processor may be further configured to, in response to the received user input, determine a switched scan mode corresponding to the changed target portion. The processor may be further configured to cause the switched scan mode to be presented on the display screen via the user interface for selection.

In some embodiments, the user input may indicate an operation for changing a scan range of the target portion corresponding to the scan mode. The processor may be further configured to, in response to the received user input, adjust the scan range. The processor may be further configured to adjust the scan mode according to the adjusted scan range. The processor may be further configured to cause the adjusted scan mode to be presented on the display screen via the user interface for confirmation.

In some embodiments, the user input indicates an operation for adjusting a scan protocol corresponding to the scan mode. The processor may be further configured to, in response to the received user input, adjust the scan protocol. The processor may be further configured to cause the adjusted scan protocol to be presented on the display screen via the user interface for confirmation.

According to a third aspect of the present disclosure, a method is provided. The method may be implemented on at least one computing device, each of which may include at least one processor and a storage device. The method may include obtaining image data of a subject including a first type of tissue and a second type of tissue. The method may include determining, based on the image data of the subject, a target portion including at least a portion of at least one of the first type of tissue or the second type of tissue. The method may also include determining, based at least in part on the target portion represented in the image data, a scan mode corresponding to the target portion. The method may further include causing an imaging device to acquire, based on the scan mode, image data of the target portion.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not scaled. These embodiments are non-limiting exemplary embodiments, in which like reference numerals represent similar structures throughout the several views of the drawings, and wherein:

FIGS. 12A-12C are schematic diagrams illustrating an exemplary process for adjusting scan protocols according to some embodiments of the present disclosure;

FIGS. 14A-14B are schematic diagrams illustrating an exemplary process for adjusting scan protocols according to some embodiments of the present disclosure; and FIGS. 15A-15B are schematic diagrams illustrating a link setting interface according to some embodiments of the present disclosure.

DETAILED DESCRIPTION

Figure 1:
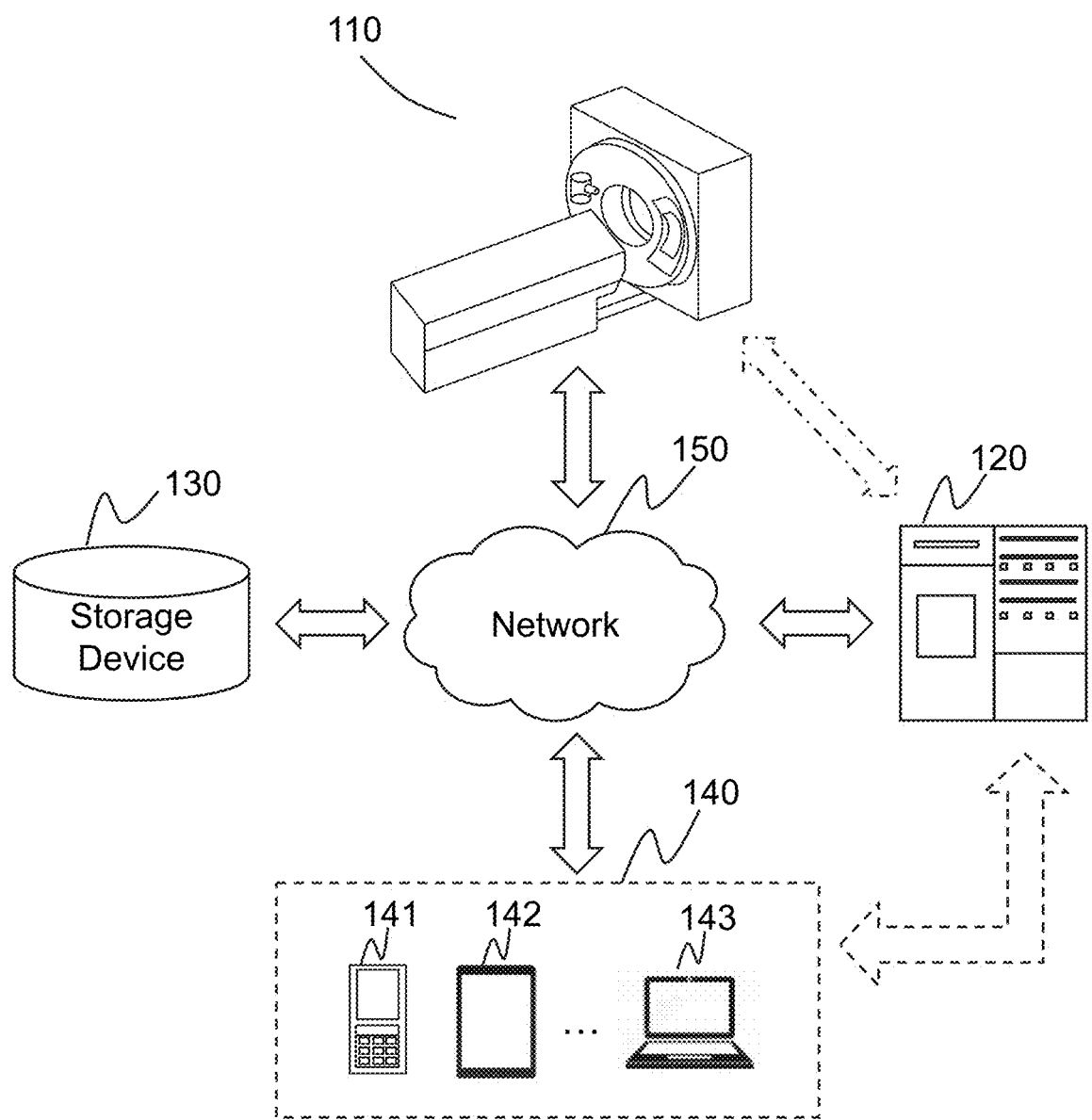
FIG. 1 is a schematic diagram illustrating an exemplary medical system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description regarding the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Provided herein are systems and methods for image data acquisition to improve its accuracy and/or efficiency by automatically determining a target portion and a scan mode. The system may include at least one storage device storing executable instructions, and at least one processor in communication with the at least one storage device. When executing the executable instructions, the at least one processor may cause the system to obtain image data of a subject including a first type of tissue and a second type of tissue. The at least one processor may also cause the system to determine the target portion including at least a portion of at least one of the first type of tissue or the second type of tissue based on the image data of the subject. The at least one processor may further cause the system to determine the scan mode corresponding to the target portion based at least in part on the target portion represented in the image data.

The at least one processor may further cause a medical device to perform the medical procedure including, e.g., obtaining image data of the target portion of the subject using an imaging device according to the scan mode.

Accordingly, the automated determination of the target portion and the corresponding scan mode, according to which the medical procedure may be performed, may render the determination independent from the clinical experience of a user, reduce the inter-user variation, and improve the efficiency and accuracy of the target portion and/or scan mode determination, which in turn may reduce the time for executing, and/or improving the accuracy and/or efficiency of the medical procedure. In addition, the user may adjust the scan mode, one or more scan parameters, a scan range, etc., which may allow flexibility for the user to operate.

FIG. 1 is a schematic diagram illustrating an exemplary medical system according to some embodiments of the present disclosure. In some embodiments, the medical system 100 may be a single-modality system or a multi-modality system. Exemplary single-modality systems may include a magnetic resonance (MR) system, a positron emission tomography (PET) system, a single-photon emission computed tomography (SPECT) system, etc. Exemplary multi-modality systems may include a magnetic resonance-positron emission tomography (MR-PET) system, a PET-CT system, etc. In some embodiments, the medical system 100 may include modules and/or components for performing imaging and/or related analysis. It should be noted that the descriptions of the MR system in the present disclosure are merely provided for illustration, and not intended to limit the scope of the present disclosure.

Merely by way of example, as illustrated in FIG. 1, the medical system 100 may include a medical device 110, a processing device 120, a storage device 130, one or more terminals 140, and a network 150. The components in the medical system 100 may be connected in one or more of various ways. Merely by way of example, the medical device 110 may be connected to the processing device 120 through the network 150. As another example, the medical device 110 may be connected to the processing device 120 directly as illustrated in FIG. 1. As a further example, the terminal(s) 140 may be connected to another component of the medical system 100 (e.g., the processing device 120) via the network 150. As still a further example, the terminal(s) 140 may be connected to the processing device 120 directly as illustrated by the dotted arrow in FIG. 1. As still a further example, the storage device 130 may be connected to another component of the medical system 100 (e.g., the processing device 120) directly as illustrated in FIG. 1, or through the network 150.

The medical device 110 may be configured to acquire image data relating to at least one part of a subject. The image data relating to at least one part of a subject may include an image (e.g., an image slice), projection data, or a combination thereof. In some embodiments, the image data may be a two-dimensional (2D) image data, a three-dimensional (3D) image data, a four-dimensional (4D) image data, or the like, or any combination thereof. The subject may be biological or non-biological. For example, the subject may include a patient, a man-made object, etc. As another example, the subject may include a specific portion, organ, and/or tissue of the patient. For example, the subject may include the spine, a vertebra, a centrum, an intervertebral disc, or the like, or any combination thereof. In some embodiments, the medical device 110 may include a single modality imaging device. For example, the medical device 110 may include a magnetic resonance imaging (MRI) device (also referred to as an MR device, an MR scanner). In some embodiments, the medical device 110 may include a multi-modality imaging device. Exemplary multi-modality imaging devices may include a PET-MRI device. For example, the medical device 110 may include a PET device and an MRI device. The MRI device may scan a subject or a portion thereof that is located within its detection region and generate projection data relating to the subject or the portion thereof. The following descriptions are provided regarding an imaging device as the medical device 110 unless otherwise stated. It should be noted that the descriptions of an MR scanner in the present disclosure are merely provided for illustration, and not intended to limit the scope of the present disclosure.

In some embodiments, the medical device 110 may include an MR signal acquisition module, an MR control module, and an MR data storage module. The MR signal acquisition module may include a magnetic unit and a radio frequency (RF) unit. The magnetic unit may mainly include a main magnet configured to generate a main magnetic field B0 and a gradient component configured to a gradient magnetic field. The main magnet included in the magnetic unit may include a permanent magnet, a superconducting electromagnet, a resistive electromagnet, etc. The gradient component may include one or more gradient current amplifiers (AMPs) and one or more gradient coils. The gradient component may further include three autonomous channels Gx, Gy, and Gz. Each gradient current amplifier may stimulate the corresponding gradient coil in the one or more gradient coils to generate a gradient magnetic field for generating a coded signal to encoding a magnetic resonance signal. The RF unit may include a RF transmitting coil and a RF receiving coil. The RF transmitting coil may be used to transmit an RF pulse signal to the subject or a portion. The RF receiving coil may be used to receive a magnetic resonance signal collected from the subject or a portion. According to different functions, the RF coil may include a volume coil and a local coil. In some embodiments, the volume coil and/or the local coil may include a cage coil, a solenoid coil, a saddle coil, a Helmholtz coil, an array coil, a loop coil, or the like, or any combination thereof. For example, the local coil may be an array coil, and the array coil may be set as a four-channel mode, an eight-channel mode, or a sixteen-channel mode. The magnetic unit and RF unit may form a magnetic resonance device with an open and low magnetic field or a closed superconducting magnetic resonance device. The MR control module may be configured to monitor the MR signal acquisition module and the MR data storage module. In some embodiments, the MR control module may receive information or pulse parameters sent by the MR signal acquisition module. In addition, the MR control module may further control the processing of an MR data processing module. In some embodiments, the MR control module may be connected with a pulse sequence generator, a gradient waveform generator, a transmitter, a receiver, or the like, or any combination. After receiving an instruction of the user from a console, the MR control module may control the magnetic field module to perform a scan sequence.

In some embodiments, the main magnet may generate the main magnetic field B0. Nucleus in the subject or a portion may generate precession frequencies under the main magnetic field. The precession frequencies may be proportional to the strength of the main magnetic field. The MR control module may store and send instructions of a scan sequence to be performed. The pulse sequence generator may control the gradient waveform generator and the transmitter based on the instructions of the scan sequence. The gradient waveform generator may output a gradient pulse signal with a certain waveform and a scheduled timing. After passing through the Gx, Gy, and Gz gradient current amplifier, the gradient pulse signal may pass through three independent channels Gx, Gy, Gz of the gradient component. Each gradient current amplifier may stimulate a corresponding gradient coil of the one or more gradient coils to generate a gradient magnetic field configured to generate the corresponding spatial coded signal to locate the MR signal. The pulse sequence generator may perform the scan sequence, and output data (including the time for transmitting an RF pulse, the strength and shape of the RF pulse, the time for receiving an RF pulse, and a length of an acquisition window) to the transmitter. At the same time, the transmitter may transmit the corresponding RF pulse to a body transmitter coil in the RF unit to generate the gradient magnetic field B1. Under the gradient magnetic field B1, a signal generated by the nucleus of the subject may be received by the receiving coil in the RF unit, and then transmitted to the MR data processing module through a transmit/receive switch. After being performed by digital processing (such as amplification, demodulation, filter, AD conversion, etc.), the signal may be transferred to the MR data storage module. The scan may end after the MR data storage module acquires raw k-space data. The raw k-space data may be reorganized into multiple sets of k-space data each of which corresponds to an MR image to be reconstructed. Each set of k-space data may be input to an array processor. The MR image may be reconstructed and combined with the magnetic resonance signal to form a group of image data.

The processing device 120 may process data and/or information obtained from the medical device 110, the terminal(s) 140, and/or the storage device 130. For example, the processing device 120 may obtain image data of a subject including a first type of tissue and a second type of tissue. The processing device 120 may determine a target portion including at least a portion of at least one of the first type of tissue or the second type of tissue based on the image data of the subject. The processing device 120 may further determine, based at least in part on the target portion represented in the image data, a scan mode corresponding to the target portion. The processing device 120 may further cause an imaging device (e.g., the medical device 110) to acquire, based on the scan mode, image data of the target portion.

In some embodiments, the processing device 120 may determine the trained machine learning model by training a machine learning model using a plurality of training samples obtained from a sample set. The trained machine learning model used in the present disclosure (e.g., the trained machine learning model) may be updated from time to time, e.g., periodically or not, based on a sample set that is at least partially different from the original sample set from which the original trained machine learning model is determined. For instance, the trained machine learning model (e.g., the trained machine learning model) may be updated based on a sample set including new samples that are not in the original sample set. In some embodiments, the determination and/or updating of the trained machine learning model (e.g., the trained machine learning model) may be performed on a processing device, while the application of the trained machine learning model may be performed on a different processing device. In some embodiments, the determination and/or updating of the trained machine learning model (e.g., the trained machine learning model) may be performed on a processing device of a system different than the medical system 100 or a server different than a server including the processing device 120 on which the application of the trained machine learning model is performed. For instance, the determination and/or updating of the trained machine learning model (e.g., the trained machine learning model) may be performed on a first system of a vendor who provides and/or maintains such a machine learning model and/or has access to training samples used to determine and/or update the trained machine learning model, while image generation based on the provided machine learning model may be performed on a second system of a client of the vendor. In some embodiments, the determination and/or updating of the trained machine learning model (e.g., the trained machine learning model) may be performed online in response to a request for image generation. In some embodiments, the determination and/or updating of the trained machine learning model may be performed offline.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal(s) 140, and/or the storage device 130 via the network 150. As another example, the processing device 120 may be directly connected to the medical device 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. The data may include image data acquired by the processing device 120, algorithms and/or models for processing the image data, etc. For example, the storage device 130 may store image data (e.g., MR images, image data of the subject, etc.) acquired by the medical device 110. As another example, the storage device 130 may store one or more algorithms for processing the image data, the anatomical model, etc. In some embodiments, the storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140, etc.). One or more components in the medical system 100 may access the data or instructions stored in the storage device 130 via the network 150. In some embodiments, the storage device 130 may be directly connected to or communicate with one or more other components in the medical system 100 (e.g., the processing device 120, the terminal(s) 140, etc.). In some embodiments, the storage device 130 may be part of the processing device 120.

The terminal(s) 140 may include a mobile device 141, a tablet computer 142, a laptop computer 143, or the like, or any combination thereof. In some embodiments, the mobile device 141 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the medical system 100. In some embodiments, one or more components of the medical device 110 (e.g., an MRI device), the terminal(s) 140, the processing device 120, the storage device 130, etc., may communicate information and/or data with one or more other components of the medical system 100 via the network 150. For example, the processing device 120 may obtain data from the medical device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

It should be noted that the above description of the medical system 100 is merely provided for illustration, and not intended to limit the scope of the present disclosure. For persons having ordinary skills in the art, multiple variations and modifications may be made under the teachings of the present disclosure. For example, the assembly and/or function of the medical system 100 may be varied or changed according to specific implementation scenarios.

Figure 2:
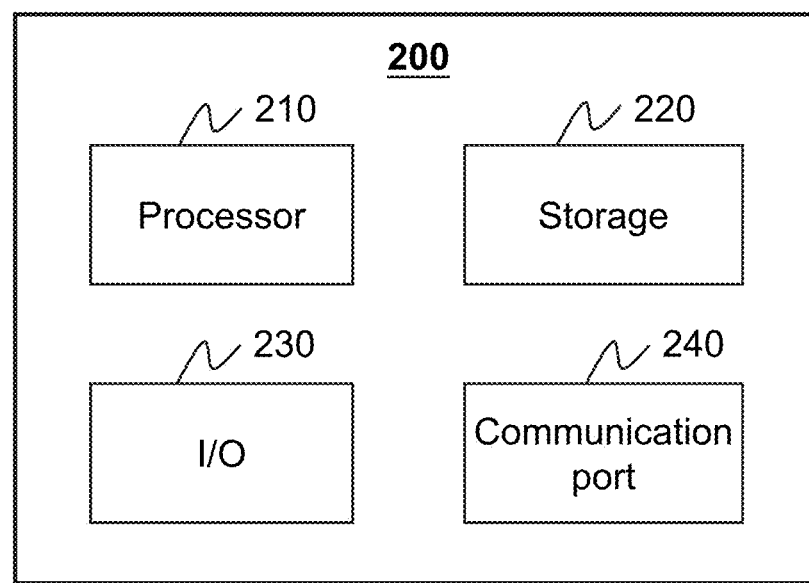
FIG. 2 is a schematic diagram illustrating hardware and/or software components of an exemplary computing device on which the processing device may be implemented according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the medical device 110, the terminal(s) 140, the storage device 130, and/or any other component of the medical system 100. Specifically, the processor 210 may process one or more measured data sets obtained from the medical device 110. For example, the processor 210 may generate an image based on the data set(s). In some embodiments, the generated image may be stored in the storage device 130, the storage 220, etc. In some embodiments, the generated image may be displayed on a display screen device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuit (ASIC), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal(s) 140, the storage device 130, or any other component of the medical system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
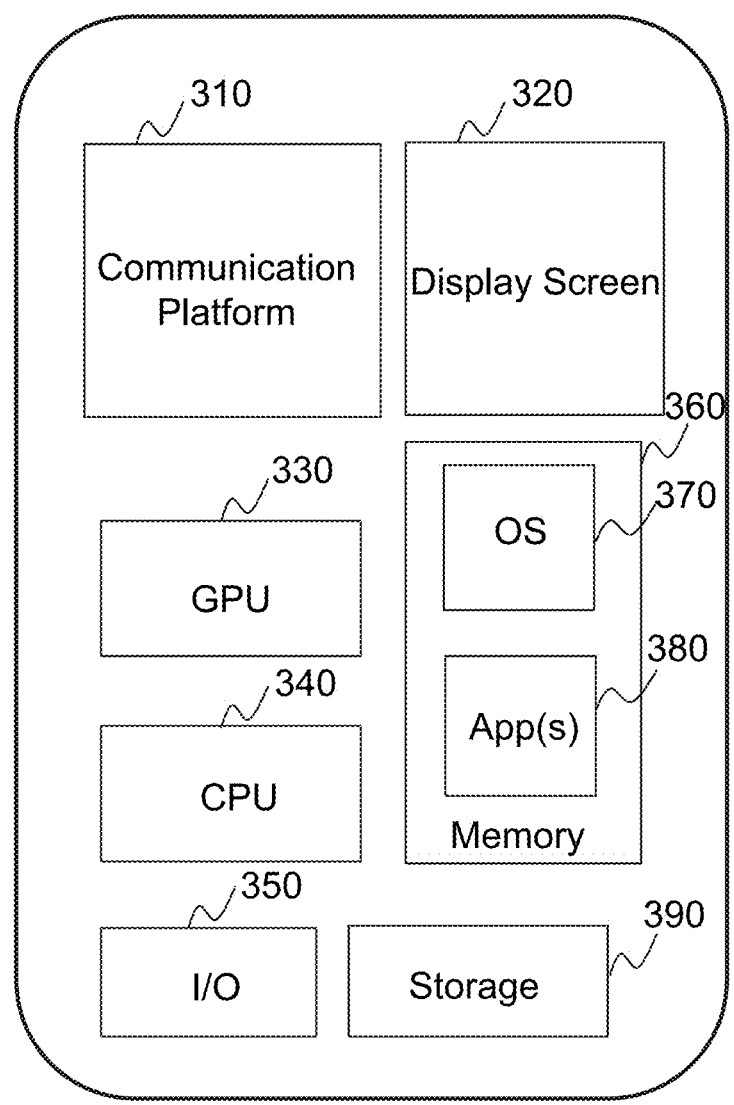
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display screen 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 to be executed by the CPU 340. The applications 380 may include a browser or any other suitable mobile apps for receiving and rendering information relating to image data acquisition or other information from the processing device 120. User interactions with the information stream may be achieved via the I/O 350 and provided to the processing device 120 and/or other components of the medical system 100 via the network 150.

To implement various modules, units, and functionalities described in the present disclosure, computer hardware platforms may be used as the hardware platform(s) for one or more of the elements described herein. The hardware elements, operating systems and programming languages of such computers are conventional, and it is presumed that those skilled in the art are adequately familiar therewith to adapt those technologies for image data acquisition as described herein. A computer with user interface elements may be used to implement a personal computer (PC) or another type of work station or terminal device, although a computer may also act as a server if appropriately programmed. It is believed that those skilled in the art are familiar with the structure, programming, and general operation of such computer equipment and as a result, the drawings should be self-explanatory.

Figure 4A:
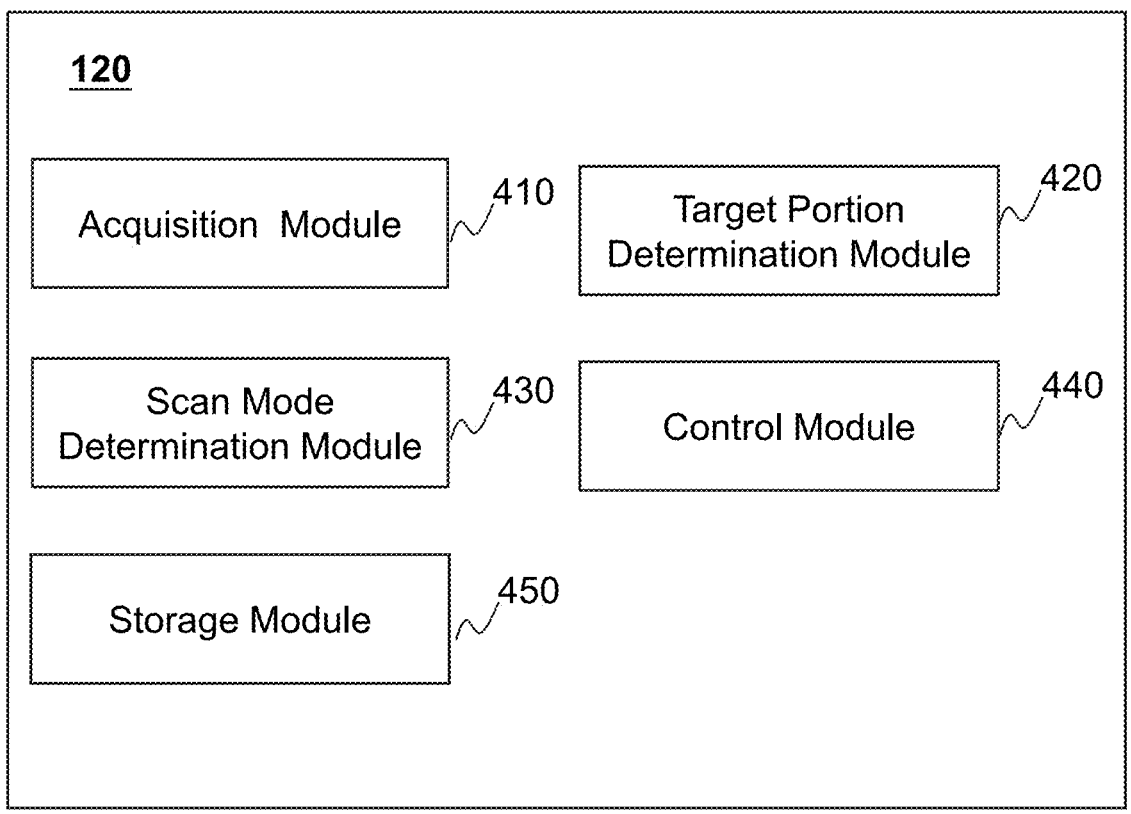
FIG. 4A is a block diagram illustrating an exemplary processing device according to some embodiments of the present disclosure.

FIG. 4A is a block diagram illustrating an exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4A, the processing device 120 may include an acquisition module 410, a target portion determination module 420, a scan mode determination module 430, a control module 440, and a storage module 450. Each of the modules described above may be a hardware circuit that is designed to perform certain actions, e.g., according to a set of instructions stored in one or more storage media, and/or any combination of the hardware circuit and the one or more storage media.

The acquisition module 410 may be configured to acquire image data of a subject including a first type of tissue and a second type of tissue. The subject may include the spine or a portion thereof (e.g., the cervical vertebra, the thoracic vertebra, the lumbar vertebra, a centrum, an intervertebral disc). In some embodiments, the subject may include the first type of tissue, the second type of tissue, a third type of tissue, etc. The image data of the subject may be configured to provide a representation of the subject. The image data acquired by the imaging device may include pre-scanning data, a scout image (or a scout image), a diagnostic image, etc. In some embodiments, the acquisition module 410 may acquire the image data of the subject from a storage device, for example, the storage device 130, or any other storage (not shown). In some embodiments, the acquisition module 410 may acquire the image data of the subject from the medical device 110.

The target portion determination module 420 may be configured to determine the target portion including at least a portion of at least one of the first type of tissue or the second type of tissue based on the image data of the subject. The first type of tissue or the second type of tissue may be defined into a plurality of groups of slices, and each group of slices may contain one or more slices. The target portion may be a portion of the subject where an anomaly exists. In some embodiments, the target portion determination module 420 may determine the target portion based on an anomaly result indicating whether an anomaly exists in at least one of the first type of tissue or the second type of tissue. In some embodiments, if the anomaly result includes that the anomaly exists in both the first type of tissue and the second type of tissue, the target portion determination module 420 may determine the target portion from the first type of tissue and the second type of tissue based further on personalized data of the subject. In some embodiments, the target portion determination module 420 may determine the anomaly result based on a segmentation technique. In some embodiments, the target portion determination module 420 may determine the anomaly result (or the target portion) based on the image data of the subject and an anatomical model. In some embodiments, the target portion determination module 420 may retrieve the anatomical model from the storage device 130, the terminal(s) 140, or any other storage device. In some embodiments, the target portion determination module 420 may input the image data of the subject into the anatomical model. An output result may be generated by the anatomical model. The output result of the anatomical model may include the marked first type of tissue and/or the marked second type of tissue identified from the image data, the anomaly result, the target portion, etc. In some embodiments, the target portion determination module 420 may input the personalized data and the image data into the anatomical model. The anatomical model may generate the output result based on the personalized data and the image data of the subject.

In some embodiments, the target portion determination module 420 may change, and/or adjust the target portion according to an input indicating an operation for changing and/or adjusting the target portion. For example, the target portion determination module 420 may receive an input indicating an operation for changing the target portion. The target portion determination module 420 may change the target portion according to the input. As another example, the target portion determination module 420 may receive an input indicating an operation for adjusting a scan range of the target portion. The target portion determination module 420 may adjust the scan range of the target portion according to the input.

The scan mode determination module 430 may determine a scan mode corresponding to the target portion based at least in part on the target portion represented in the image data. The scan mode may be defined by one or more parameters. The one or more parameters of the scan mode may include one or more scan angles, a count of scan slices corresponding to each of the one or more scan angles, a position of each of the scan slices, or the like, or any combination thereof. The scan mode may include a first type (also referred to as a first scan mode) or a second type (also referred to as a second scan mode) according to the count of the one or more scan angles. The first scan mode may include a parallel scan with a plurality of groups of slices oriented at a single angle (or the same angle). The second scan mode may include an interleaved scan with a plurality of groups of slices oriented at different angles.

In some embodiments, the scan mode determination module 430 may determine the type of the scan mode and/or the one or more parameters of the scan mode. In some embodiments, after the determination of the target portion, the scan mode determination module 430 may determine the type of the scan mode corresponding to the target portion based on the target portion. If the target portion includes the first type of tissue (e.g., one or more vertebrae), the scan mode determination module 430 may determine the first scan mode corresponding to the target portion including the first type of tissue. The scan mode determination module 430 may further determine the one or more parameters of the first scan mode based on the characteristics of the target portion identified from the image data. Further, the parallel scan may be such that the plurality of scan slices corresponding to the one single scan angle are perpendicular to the long axis of the first type of tissue or parallel to the short axis of the first type of tissue.

If the target portion includes the second type of tissue (e.g., the one or more intervertebral discs), the scan mode determination module 430 may determine the second scan mode corresponding to the target portion including the second type of tissue. the scan mode determination module 430 may further determine the one or more parameters of the second scan mode based on the characteristics of the target portion identified from the image data. Further, the interleaved scan may be such that the each group of slices containing a plurality of slices oriented at one of a plurality of different angles.

In some embodiments, the scan mode determination module 430 may change, switch, and/or adjust the scan mode according to an input indicating an operation for changing and/or adjusting the scan mode. For example, the scan mode determination module 430 may receive an input indicating an operation for switching the scan mode. The scan mode determination module 430 may switch the scan mode according to the input. As another example, the scan mode determination module 430 may receive an input indicating an operation for adjusting one or more parameters of the scan mode. The scan mode determination module 430 may adjust the one or more parameters of the scan mode according to the input.

The control module 440 may be configured to cause an imaging device to acquire, based on the scan mode, image data of the target portion. In some embodiments, the control module 440 may determine one or more parameters of a scan sequence (also referred to as a pulse sequence) based on the scan mode. In some embodiments, the control module 440 may determine one or more parameters of a scan sequence (also referred to as a pulse sequence) based on the scan mode according to a default setting of the medical system 100. Then the control module 440 may transmit the one or more parameters of the scan sequence to the medical device 110 to acquire the image data of the subject. The medical device 110 may perform the scanning of the subject according to the scan sequence.

The storage module 450 may be configured to store data and/or instructions associated with the medical system 100. For example, the storage module 450 may store data of the image data of the subject, the target portion, the anatomical model, the personalized data, the output result, the scan mode, the image data of the target portion etc. In some embodiments, the storage module 450 may be the same as the storage device 130 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the acquisition module 410 and the control module 440 may be integrated into a single module.

As another example, some other components/modules may be added into and/or omitted from the processing device 120.

Figure 4B:
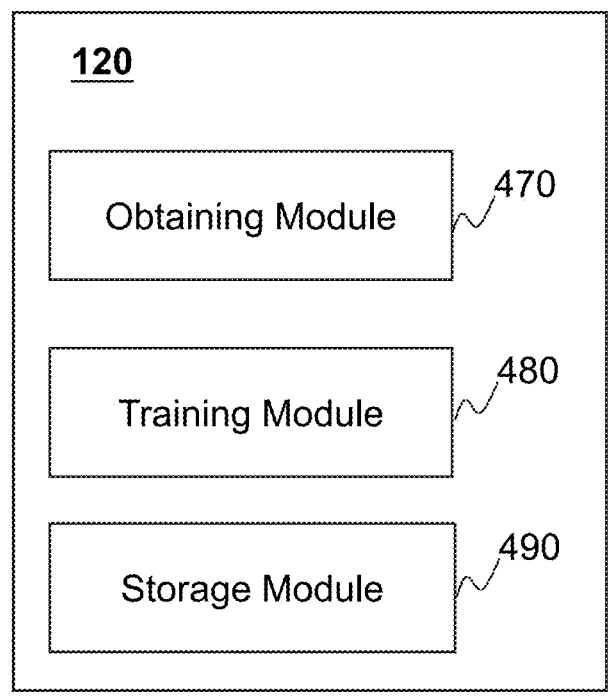
FIG. 4B is a block diagram illustrating an exemplary processing device according to some embodiments of the present disclosure.

FIG. 4B is a block diagram illustrating another exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4B, the processing device 120 may include an obtaining module 470, a training module 480, and a storage module 490. Each of the modules described above may be a hardware circuit that is designed to perform certain actions, e.g., according to a set of instructions stored in one or more storage media, and/or any combination of the hardware circuit and the one or more storage media.

The obtaining module 470 may be configured to obtain a plurality of training samples. Each of the plurality of training samples may include image data of a sample subject.

The image data of the sample subject may be a scout image, such as a three-dimensional scout image, a two-dimensional scout image (e.g., a sagittal scout image). The sample subject may include the first type of tissue and the second type of tissue. As used herein, the first type of tissue refers to one or more vertebrae and the second type of tissue refers to one or more intervertebral discs.

In some embodiments, each of the plurality of training samples may include annotated image data of the sample subject. In some embodiments, the image data of the sample subject corresponding to each of the training samples may be annotated by identifying the first type of tissue and/or the second type of tissue, an anomaly, a target portion, etc. The identification of the first type of tissue and/or the second type of tissue, the anomaly result, the target portion, etc. may include locating and/or marking the first type of tissue and/or the second type of tissue, the anomaly, the target portion, etc. from the image data of the sample subject. The image data of the sample subject may be used as input in the training process of a machine learning model. The annotated image data of the sample subject may be used as a reference output corresponding to the image data of the sample subject in the training process of the machine learning model. The first type of tissue and/or the second type of tissue, the anomaly, the target portion, etc. may be identified manually or automatically.

In some embodiments, each of the plurality of training samples may include the image data of the sample subject and personalized data of the sample subject. The personalized data of the sample subject may include age, gender, occupation, medical history, etc. The image data and personalized data of the sample subject may be used as input in the training process of a machine learning model. The annotated image data of the sample subject may be used as a reference output corresponding to the image data and personalized data of the sample subject in the training process of the machine learning model.

The training module 480 may be configured to generate a trained machine learning model by training a machine learning model using the plurality of training samples in a training process. In some embodiments, the training module 480 may construct the trained machine learning model based on a deep learning model (e.g., a convolutional neural network (CNN) model, a deep belief nets (DBN) machine learning model, a stacked auto-encoder network), a recurrent neural network (RNN) model, a long short term memory (LSTM) network model, a fully convolutional neural network (FCN) model, a generative adversarial network (GAN) model, a back propagation (BP) machine learning model, a radial basis function (RBF) machine learning model, an Elman machine learning model, or the like, or any combination thereof. The training module 480 may train the machine learning model based on the plurality of training samples using a training algorithm. In some embodiments, the training module 480 may perform a plurality of iterations to iteratively update one or more parameter values of the machine learning model to obtain the trained machine learning model. Before the plurality of iterations, the training module 480 may initialize the parameter values of the machine learning model.

The storage module 490 may be configured to store data and/or instructions associated with the medical system 100. For example, the storage module 490 may store data of the plurality of training samples (e.g., the training samples), one or more machine learning models, the anatomical model, etc. In some embodiments, the storage module 490 may be the same as the storage device 130 and/or the storage module 450 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the obtaining module 470 and the storage module 490 may be integrated into a single module. As another example, some other components/modules may be added into the processing device 120.

Figure 5:
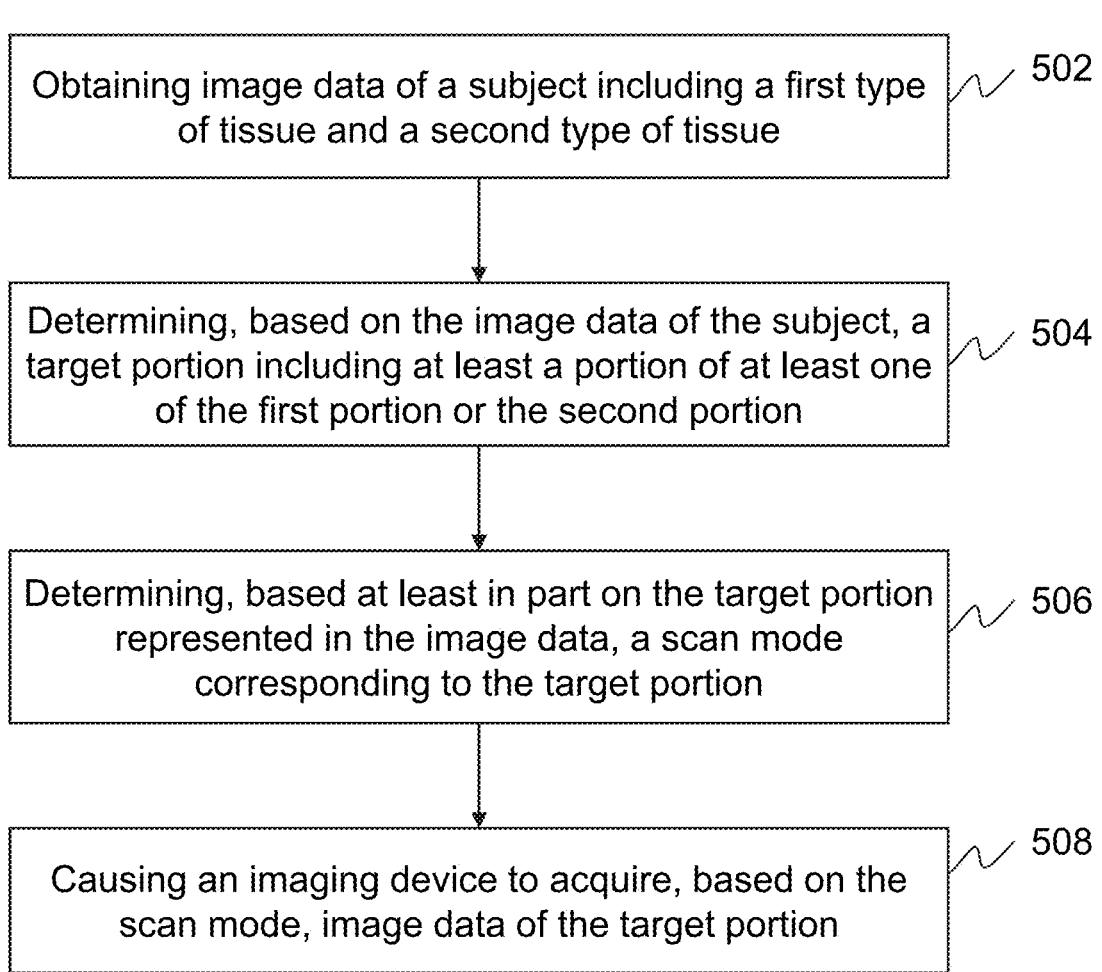
FIG. 5 is a flowchart illustrating an exemplary process for image data acquisition according to some embodiments of the present disclosure.

FIG. 5 is a flowchart illustrating an exemplary process for image data acquisition according to some embodiments of the present disclosure. In some embodiments, process 500 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 502, the processing device 120 (e.g., the acquisition module 410) may acquire image data of a subject including a first type of tissue and a second type of tissue.

The subject may be biological or non-biological. For example, the subject may include a patient, a man-made object, etc. As another example, the subject may include a specific portion, organ, and/or tissue of a patient. As a further example, the subject may include the spine or a portion thereof (e.g., the cervical vertebra, the thoracic vertebra, the lumbar vertebra, a centrum, an intervertebral disc). In some embodiments, the subject may include the first type of tissue, the second type of tissue, a third type of tissue, etc. The first type of tissue, the second type of tissue, and the third type of tissue, etc., may be different according to different subjects. For example, when the subject includes the spine, the first type of tissue may include one or more vertebrae; the second type of tissue may include one or more intervertebral disc; the third type of tissue may include the spinal cord in the spine. When the subject includes a leg, the first type of tissue may include a bone (e.g., the tibia, the perone bone, etc.). The second type of tissue may include a joint (e.g., a knee joint, an ankle joint, etc.).

The image data of the subject may be configured to provide a representation of the subject. In some embodiments, the image data of the subject may include a three-dimensional image. In some embodiments, the image data of the subject may include a two-dimensional image in a sagittal view, a transversal view, a coronal view, etc. The image data acquired by the imaging device may include pre-scanning data, a scout image (or a scout image), a diagnostic image, etc.

In some embodiments, the pre-scanning data may be acquired by the imaging device via scanning the subject according to a fast pre-scanning sequence (also referred to as a fast pre-scanning pulse sequence). Exemplary fast pre-scanning sequences may include a low-resolution magnetic resonance sequence, a fast pulse sequence, etc. For example, the fast pulse sequence may include a 3D gradient recalled echo (GRE) sequence, a single-shot fast spin-echo (SSFSE) sequence, etc.

In some embodiments, the scout image may be acquired by the imaging device via scanning the subject according to a positioning scanning technique. Exemplary positioning scanning techniques may include using camera imaging, infrared imaging, a positioning scanning sequence (e.g., a low-resolution magnetic resonance sequence), etc.

In some embodiments, the diagnostic image may be acquired by the imaging device (e.g., an MR scanner) via scanning the subject according to an imaging sequence (e.g., a spin-echo (SE) sequence, a fast SE sequence, an echo planer imaging (EPI) sequence, etc.). The diagnostic image may be a historical image acquired by the imaging device via scanning the same subject and stored in the storage device, for example, the storage device 130, or any other storage (not shown).

In some embodiments, the processing device 120 (e.g., the acquisition module 410) may obtain the image data of the subject from a storage device, for example, the storage device 130, or any other storage (not shown). For example, the medical device 110 may acquire the image data of the subject and store the acquired image data of the subject in the storage device. The processing device 120 may obtain the image data of the subject from a storage device. In some embodiments, the processing device 120 may obtain the image data of the subject from the medical device 110. For example, the medical device 110 may acquire the image data of the subject and transmit the acquired image data of the subject to the processing device 120. In some embodiments, the processing device 120 (e.g., the acquisition module 410) may reconstruct the image data of the subject (e.g., a scout image of the subject) based on scan data (e.g., k-space data, projection data, etc.).

In 504, the processing device 120 (e.g., the target portion determination module 420) may determine the target portion including at least a portion of at least one of the first type of tissue or the second type of tissue based on the image data of the subject.

The target portion may be a portion of the subject where an anomaly exists. The anomaly may include a pathological change or lesion (e.g., nodules, a tumor, trauma, radiation injury) that exists in the subject. For example, when the subject includes the spine, the anomaly may include a vertebrae injury, intervertebral disc herniation, intervertebral disc prolapse, a tumor in the spinal cord, etc.

In some embodiments, the processing device 120 may determine the target portion based on an anomaly result indicating whether an anomaly exists in at least one of the first type of tissue or the second type of tissue. If the anomaly result includes that the anomaly exists in the first type of tissue, the processing device 120 may determine that the target portion includes the first type of tissue. If the anomaly result includes that the anomaly exists in the second type of tissue, the processing device 120 may determine that the target portion includes the second type of tissue. In some embodiments, if the anomaly result includes that the anomaly exists in both the first type of tissue and the second type of tissue, the processing device 120 may determine that the target portion includes both the first type of tissue and the second type of tissue.

In some embodiments, if the anomaly result includes that the anomaly exists in both the first type of tissue and the second type of tissue, the processing device 120 may determine the target portion from the first type of tissue and the second type of tissue based further on personalized data of the subject. The personalized data of the subject may include age, gender, occupation, medical history, etc. In some embodiments, the first type of tissue may include one or more vertebrae, and the second type of tissue may include one or more intervertebral discs. Many middle-aged and elderly people may suffer from problems associated with intervertebral discs (e.g., intervertebral disc herniation, intervertebral disc prolapse, etc.), while young people or children may be less likely. If the processing device 120 determines that the anomaly exists in the one or more intervertebral discs and one or more vertebrae, and the age of the subject exceeds a threshold (e.g., 30, 35, 40, 45, 50, etc.), the processing device 120 may determine that the target portion includes the one or more intervertebral discs. If the age of the subject is less than a threshold (e.g., 10, 9, 5, etc.), the processing device 120 may determine that the target portion includes the one or more vertebrae.

In some embodiments, the processing device 120 may determine the anomaly result based on a segmentation technique. Exemplary segmentation techniques may include a region-based segmentation, an edge-based segmentation, a wavelet transform segmentation, a mathematical morphology segmentation, an artificial neural network-based segmentation, a genetic algorithm-based segmentation, or the like, or a combination thereof. For example, the processing device 120 may segment a region in the image data that includes a tumor using a segmentation technique. The processing device 120 may determine that the anomaly exists in the region. If the segmented region is in the first type of tissue, the processing device 120 may determine that the anomaly exists in the first type of tissue. If the segmented region is in the second type of tissue, the processing device 120 may determine that the anomaly exists in the second type of tissue. As another example, the processing device 120 may segment one or more regions presenting the second type of tissue (e.g., an intervertebral disc) and/or the first type of tissue (e.g., a vertebra) from the image data using a segmentation technique. The processing device 120 may determine one or more characteristics (e.g., orientation, shape, size, etc.) of the second type of tissue and/or the first type of tissue (e.g., a vertebra) based on the image data. The processing device 120 may determine whether the anomaly exists in the second type of tissue and/or the first type of tissue (e.g., a vertebra) based on the one or more characteristics (e.g., orientation, shape, size, etc.) identified from the image data and corresponding reference characteristics (e.g., reference orientation, reference shape, reference size, etc.).

In some embodiments, the processing device 120 (e.g., the target portion determination module 420) may determine the anomaly result (or the target portion) based on the image data of the subject and an anatomical model. In some embodiments, the processing device 120 may retrieve the anatomical model from the storage device 130, the terminals(s) 140, or any other storage device. For example, the anatomical model may be determined by training a machine learning model offline based on a plurality of training samples using the processing device 120 or a processing device other than the processing device 120. The anatomical model may be stored in the storage device 130, the terminals(s) 140, or any other storage device. For instance, the processing device 120 may retrieve the anatomical model from the storage device 130, the terminals(s) 140, or any other storage device in response to receipt of a request for image data acquisition. More descriptions regarding the determination of the anatomical model may be performed according to process 600.

In some embodiments, the processing device 120 may input the image data of the subject into the anatomical model. An output result may be generated by the anatomical model. The output result of the anatomical model may include the marked first type of tissue and/or the marked second type of tissue identified from the image data, the anomaly result, the target portion, etc. For example, the anatomical model may directly output the target portion including the first type of tissue and/or the second type of tissue. As another example, the output result of the anatomical model may include the anomaly result indicating that the anomaly exists in the first type of tissue, the anomaly exists in the second type of tissue, the anomaly exists in the first type of tissue and the second type of tissue, or no anomaly detected.

In some embodiments, the processing device 120 may input the personalized data and the image data into the anatomical model. The anatomical model may generate the output result based on the personalized data and the image data of the subject. For example, when the anomaly exists in the first type of tissue and the second type of tissue, and the age of the subject exceeds a preset age threshold (e.g., 30, 35, 40, 45, 50, etc.), the anatomical model may output the target portion including the second type of tissue (e.g., the one or more intervertebral discs). When the anomaly exists in both the first type of tissue and the second type of tissue, and the age of the subject does not exceed the preset age threshold (e.g., 30, 35, 40, 45, 50, etc.), the anatomical model may output the target portion including the first type of tissue.

In 506, the processing device 120 (e.g., the scan mode determination module 430) may determine a scan mode corresponding to the target portion based at least in part on the target portion represented in the image data.

The scan mode may be defined by one or more parameters. The one or more parameters of the scan mode may include one or more scan angles, a count of scan slices corresponding to each of the one or more scan angles, a position of each of the scan slices, or the like, or any combination thereof. A scan angle may be used to describe a direction of a scan slice corresponding to the scan angle with respect to a reference direction (e.g., the horizontal direction, the vertical direction, etc.). A scan angle of a scan slice may relate to a shape or orientation of the target portion. The count of scan slices corresponding to each of the one or more scan angles may relate to a size of the target portion. The position of each of the scan slices may correspond to a position of a part of the target portion that corresponds to the scan slice. The scan mode may include a first type (also referred to as a first scan mode) or a second type (also referred to as a second scan mode) according to the count of the one or more scan angles. The first scan mode may include a parallel scan with a plurality of groups of slices oriented at a single angle. In other words, all the scan slices for the target portion may be in the same direction. The second scan mode may include an interleaved scan with a plurality of groups of slices oriented at different angles. For example, the target portion (e.g., multiple intervertebral discs) may include multiple parts. Each of the multiple parts may correspond to a scan angle.

Figure 9:
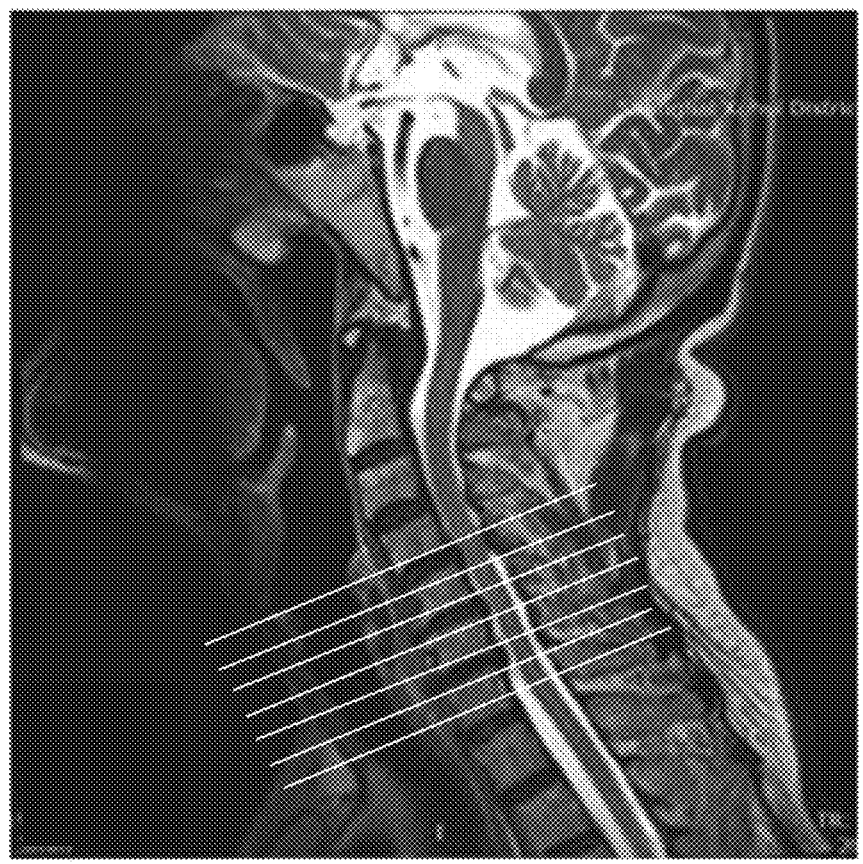
FIG. 9 is a diagram illustrating an exemplary first scan mode according to some embodiments of the present disclosure.

The determining a scan mode corresponding to the target portion may include determining the type of the scan mode and the one or more parameters of the scan mode. In some embodiments, after the determination of the target portion, the processing device 120 (e.g., the scan mode determination module 430) may determine the type of the scan mode corresponding to the target portion based on the target portion. If the target portion includes the first type of tissue (e.g., one or more vertebrae), the processing device 120 may determine the first scan mode corresponding to the target portion including the first type of tissue. The processing device 120 may further determine the one or more parameters of the first scan mode based on the characteristics of the target portion identified from the image data. For example, the processing device 120 may determine the count of the scan slices based on the size of the target portion, an input of a user (or user input for brevity), or according to a default setting of the medical system 100. As another example, the processing device 120 may determine the one single scan angle and the position of each scan slice based on the position, shape and/or the orientation of the first type of tissue. Further, the one single scan angle may be such that the plurality of scan slices corresponding to the one single scan angle are perpendicular to the long axis of the first type of tissue or parallel to the short axis of the first type of tissue. For example, FIG. 9 shows a diagram illustrating an image of the spine according to some embodiments of the present disclosure. The target portion includes the one or more vertebrae of the neck. The processing device 120 may determine the first scan mode that includes one single scan angle and six scan slices corresponding to the one single scan angle as shown in FIG. 9. The six scan slices corresponding to the same scan angle are parallel to an intervertebral disc of the neck.

Figure 10:
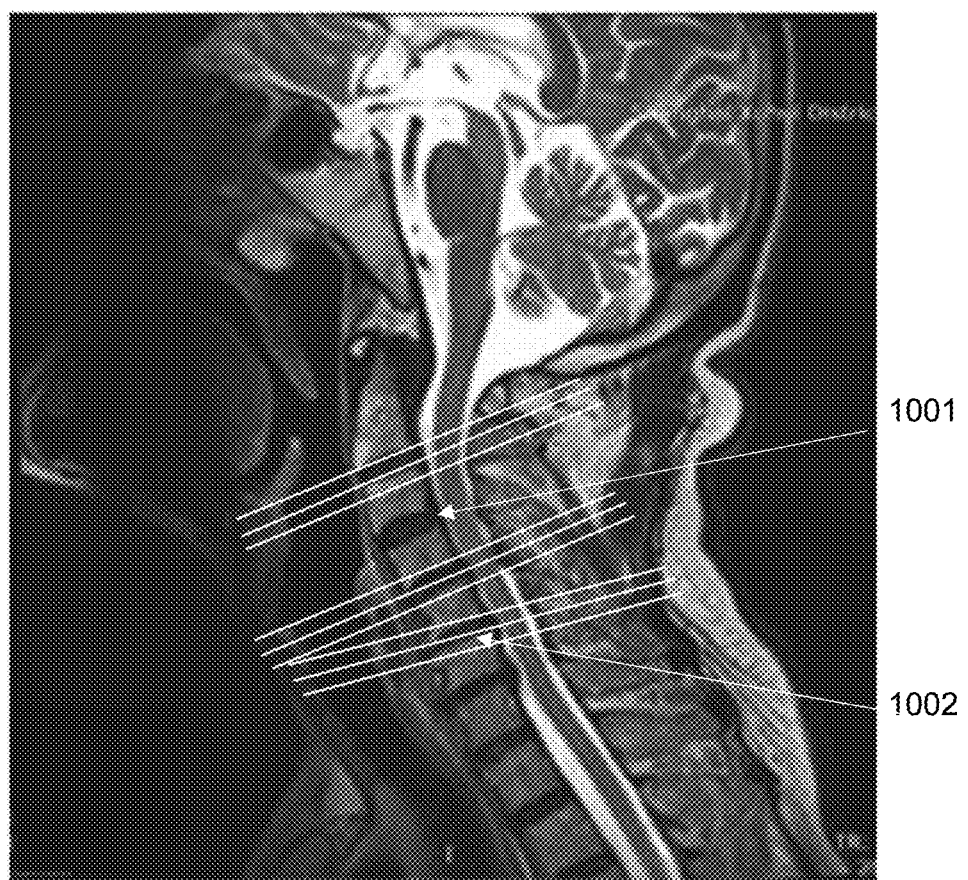
FIG. 10 is a diagram illustrating an exemplary second scan mode according to some embodiments of the present disclosure.

If the target portion includes the second type of tissue (e.g., the one or more intervertebral discs), the processing device 120 may determine the second scan mode corresponding to the target portion including the second type of tissue. The processing device 120 may further determine the one or more parameters of the second scan mode based on the characteristics of the target portion identified from the image data. For example, the processing device 120 may determine the count of the scan slices corresponding to one of the multiple scan angles based on the size of the target portion, an input of a user, or according to a default setting of the medical system 100. As another example, the processing device 120 may determine the multiple scan angles based on different portions (e.g., intervertebral discs) of the second type of tissue. Further, one of the multiple scan angles may be such that the plurality of scan slices corresponding to the one of the multiple scan angles are perpendicular to the long axis of a portion of the second type of tissue or parallel to the short axis of the portion of the second type of tissue. For example, FIG. 10 shows a diagram illustrating an image of the spine according to some embodiments of the present disclosure. The target portion includes the multiple intervertebral discs in the neck. The processing device 120 may determine the second scan mode that includes three scan angles and three scan slices corresponding to each of the three scan angles as shown in FIG. 10. The three scan slices corresponding to each of the three scan angles are parallel to an intervertebral disc of the neck.

In 508, the processing device 120 (e.g., the control module 440) may cause an imaging device to acquire, based on the scan mode, image data of the target portion. The imaging device may be configured to acquire image data of the target portion. More descriptions regarding the imaging device may be found in FIG. 1 and the descriptions thereof.

In some embodiments, the processing device 120 may determine one or more parameters of a scan sequence (also referred to as a pulse sequence) based on the scan mode. The one or more parameters of the scan sequence may include n RF pulses (e.g., the number of excitations (NEX), a bandwidth, etc.) emitted by an RF coil, parameters relating to gradient fields generated by the gradients coils, and parameters relating to MR signals (e.g., an echo time (TE), an echo train length (ETL), a spin echo type, the number of phases), etc. In some embodiments, the one or more parameters may include slice thickness, an imaging type (e.g., T1 weighted imaging, T2 weighted imaging, proton density-weighted imaging, etc.), T1, T2, an acquisition time (TA), an inversion time, or the like, or a combination thereof. The processing device 120 may determine one or more parameters of a scan sequence (also referred to as a pulse sequence) based on the scan mode according to a default setting of the medical system 100. For example, the processing device 120 may determine the parameters relating to gradient fields based on the position of the scan slices for slice selection. As another example, the processing device 120 may determine the slice thickness based on the counts of the scan slices. Then the processing device 120 may transmit the one or more parameters of the scan sequence to the medical device 110 to acquire the image data of the subject. The medical device 110 may perform the scanning of the subject according to the scan sequence. More descriptions for the image data acquisition based on the scan sequence may be found in FIG. 1 and the descriptions thereof.

In some embodiments, the target portion may be changed after the target portion is determined in operation 504. For example, if the anomaly exists in the first type of tissue, and the target portion includes the first type of tissue, the processing device 120 may deem that the target portion has changed to the second type of tissue according to an input indicating changing the target portion. The processing device 120 (e.g., the target portion determination module 420) may receive the input indicating a change in the target portion and determine a switched scan mode corresponding to the changed target portion. More descriptions regarding the switching of the scan mode may be found in FIG. 7.

In some embodiments, a scan range of the target portion may be changed. For example, the processing device 120 (e.g., the target portion determination module 420) may receive an input indicating an operation for changing a scan range of the target portion and adjust the scan range. In some embodiments, at least one of the one or more parameters of the scan mode corresponding to the target portion may be adjusted according to an input of the user or according to a default setting of the medical system. For example, the processing device 120 (e.g., the scan mode determination module 430) may receive an input indicating an operation for adjusting at least one of the one or more parameters of the scan mode corresponding to the target portion and adjust the at least one of the one or more parameters. More descriptions regarding the adjustment of the scan mode may be found in FIG. 8.

In some embodiments, when the scan range and/or the scan mode are adjusted, one or more scan protocols corresponding to the scan range and/or the scan mode may need to be adjusted. More descriptions for adjusting scan protocols may be found in FIG. 13.

In some embodiments, after acquiring the image data of the target portion, the processing device 120 may perform a reconstruction operation to obtain a magnetic resonance (MR) image of the target portion. In some embodiments, the reconstruction operation may be used to reconstruct the image data of the target portion using a Fourier transform algorithm, an algorithm based on deep learning, or the like, or any combination thereof.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 502 and operation 504 may be combined into a single operation. As another example, one or more other optional operations (e.g., a storing operation) may be added elsewhere in the process 500. In the storing operation, the processing device 120 may store information and/or data (e.g., the image data of the subject, the anatomical model, the target portion, the scan mode, image data of the target portion, etc.) associated with the medical system 100 in a storage device (e.g., the storage device 130) disclosed elsewhere in the present disclosure.

Figure 6:
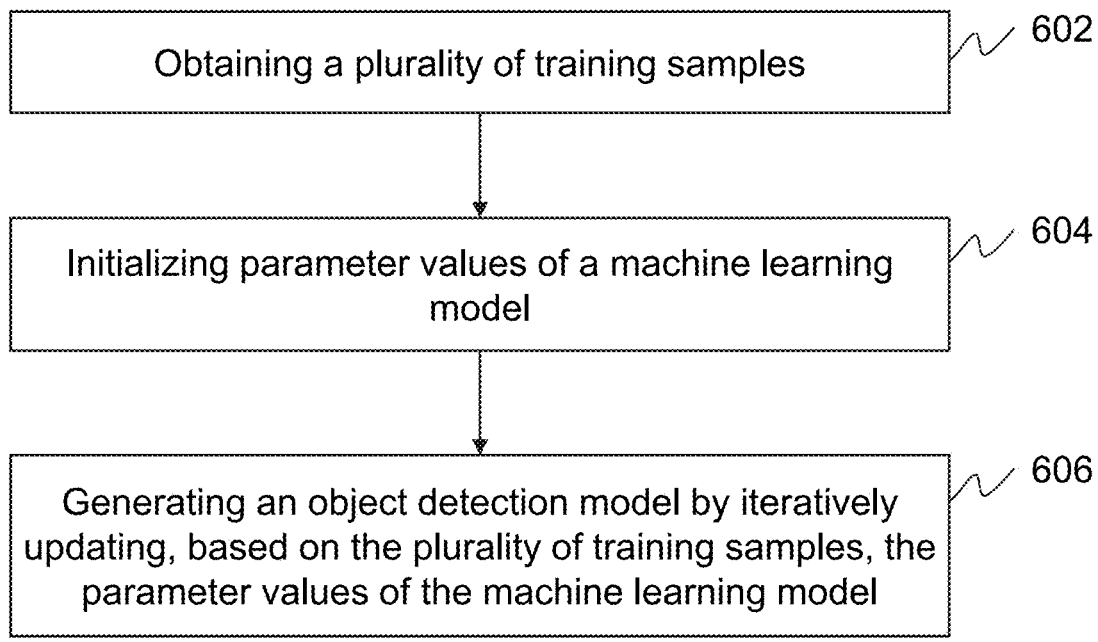
FIG. 6 is a flowchart illustrating an exemplary process for training an anatomical model according to some embodiments of the present disclosure.

FIG. 6 is a flowchart illustrating an exemplary process for training an anatomical model according to some embodiments of the present disclosure. In some embodiments, process 600 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, the trained machine learning model as described in FIG. 5 may be obtained according to the process 600. The trained machine learning model may be obtained based on a supervised learning technique, an unsupervised learning technique, a semi-supervised learning technique, or a combination thereof. It should be noted that the descriptions of the training in the present disclosure are merely provided for illustration, and not intended to limit the scope of the present disclosure.

In 602, the processing device 120 (e.g., the obtaining module 470) may obtain a plurality of training samples. Each of the plurality of training samples may include image data of a sample subject. The following descriptions of FIG. 6 are provided with reference to image data relating to the spine unless otherwise stated. It is understood that this is for illustration purposes and not intended to be limiting.

The image data of the sample subject may be a scout image, such as a three-dimensional scout image, a two-dimensional scout image (e.g., a sagittal scout image). The sample subject may include the first type of tissue and the second type of tissue. As used herein, the first type of tissue refers to one or more vertebrae and the second type of tissue refers to one or more intervertebral discs. More descriptions for the image data of the subject may be found elsewhere in the present disclosure.

In some embodiments, each of the plurality of training samples may include annotated image data of the sample subject. In some embodiments, the image data of the sample subject corresponding to each of the training samples may be annotated by identifying the first type of tissue and/or the second type of tissue, an anomaly, a target portion, etc. The identification of the first type of tissue and/or the second type of tissue, the anomaly result, the target portion, etc. may include locating and/or marking the first type of tissue and/or the second type of tissue, the anomaly, the target portion, etc. from the image data of the sample subject. The image data of the sample subject may be used as input in the training process of a machine learning model. The annotated image data of the sample subject may be used as a reference output corresponding to the image data of the sample subject in the training process of the machine learning model. The first type of tissue and/or the second type of tissue, the anomaly, the target portion, etc. may be identified manually or automatically. For example, the processing device 120 may identify the first type of tissue and/or the second type of tissue, the anomaly, the target portion, etc. using a segmentation technique, such as a region-based segmentation, an edge-based segmentation, a wavelet transform segmentation, a mathematical morphology segmentation, an artificial neural network-based segmentation, a genetic algorithm-based segmentation, etc.

In some embodiments, each of the plurality of training samples may include the image data of the sample subject and personalized data of the sample subject. The personalized data of the sample subject may include age, gender, occupation, medical history, etc. The image data and personalized data of the sample subject may be used as input in the training process of a machine learning model. The annotated image data of the sample subject may be used as a reference output corresponding to the image data and personalized data of the sample subject in the training process of the machine learning model.

In 604, the processing device 120 (e.g., the training module 480) may initialize parameter values of a machine learning model.

In some embodiments, the machine learning model to be trained may include a deep learning model (e.g., a convolutional neural network (CNN) model, a deep belief nets (DBN) machine learning model, a stacked auto-encoder network), a recurrent neural network (RNN) model, a long short term memory (LSTM) network model, a fully convolutional neural network (FCN) model, a generative adversarial network (GAN) model, a back propagation (BP) machine learning model, a radial basis function (RBF) machine learning model, an Elman machine learning model, or the like, or any combination thereof. It should be noted that the descriptions of the machine learning model in the present disclosure are merely provided for illustration, and not intended to limit the scope of the present disclosure. In some embodiments, the machine learning model may include a multi-layer structure. For example, the machine learning model may include an input layer, an output layer, and one or more hidden layers between the input layer and the output layer. In some embodiments, the hidden layers may include one or more convolution layers, one or more rectified-linear unit layers (ReLU layers), one or more pooling layers, one or more fully connected layers, or the like, or any combination thereof. As used herein, a layer of a model may refer to an algorithm or a function for processing input data of the layer. Different layers may perform different kinds of processing on their respective input. A successive layer may use output data from a previous layer of the successive layer as input data. In some embodiments, the convolutional layer may include a plurality of kernels, which may be used to extract a feature. In some embodiments, each kernel of the plurality of kernels may filter a portion (i.e., a region). The pooling layer may take an output of the convolutional layer as an input. The pooling layer may include a plurality of pooling nodes, which may be used to sample the output of the convolutional layer, so as to reduce the computational load of data processing and accelerate the speed of data processing speed. In some embodiments, the size of the matrix representing the inputted data may be reduced in the pooling layer. The fully connected layer may include a plurality of neurons. The neurons may be connected to the pooling nodes in the pooling layer. In the fully connected layer, a plurality of vectors corresponding to the plurality of pooling nodes may be determined based on a training sample, and a plurality of weighting coefficients may be assigned to the plurality of vectors. The output layer may determine an output based on the vectors and the weighting coefficients obtained from the fully connected layer.

In some embodiments, each of the layers may include one or more nodes. In some embodiments, each node may be connected to one or more nodes in a previous layer. The number of nodes in each layer may be the same or different. In some embodiments, each node may correspond to an activation function. As used herein, an activation function of a node may define an output of the node given input or a set of inputs. In some embodiments, each connection between two of the plurality of nodes in the initial machine learning model may transmit a signal from one node to another node. In some embodiments, each connection may correspond to a weight. As used herein, a weight corresponding to a connection may be used to increase or decrease the strength or impact of the signal at the connection.

The machine learning model may include a plurality of parameters, such as architecture parameters, learning parameters, etc. Exemplary architecture parameters of the machine learning model may include the size of a kernel of a layer, the total count (or number) of layers, the count (or number) of nodes in each layer, a learning rate, a batch size, an epoch, etc. Exemplary learning parameters may include a connected weight between two connected nodes, a bias vector relating to a node, etc.). Before the training, the machine learning model may have one or more initial parameter values. In the training of the machine learning model, learning parameters of the machine learning model may be updated. Before the updating process, values of the learning parameters of the machine learning model may be initialized. For example, the connected weights and/or the bias vector of nodes of the initial machine learning model may be initialized by assigning random values in a range, e.g., the range from−1 to 1. As another example, all the connected weights of the initial machine learning model may be assigned the same value in the range from−1 to 1, for example, 0. As still an example, the bias vector of nodes in the initial machine learning model may be initialized by assigning random values in a range from 0 to 1. In some embodiments, the parameters of the initial machine learning model may be initialized based on a Gaussian random algorithm, a Xavier algorithm, etc.

In 606, the processing device 120 (e.g., the training module 480) may generate the anatomical model by iteratively updating, based on the plurality of training samples, the parameter values of the machine learning model.

In the training of the machine learning model, the processing device 120 may iteratively update the parameter value(s) of the machine learning model based on the plurality of training samples. The updating of the learning parameters of the machine learning model may be also referred to as updating the machine learning model. For example, the processing device 120 may update the model parameter(s) of the machine learning model by performing one or more iterations until a termination condition is satisfied. The termination condition may indicate whether the machine learning model is sufficiently trained. The termination condition may relate to a cost function or an iteration count of the training process. For example, the processing device 120 may determine a loss function of the machine learning model and determine a value of the cost function based on the difference between an estimated output and an actual output or desired output (i.e., reference output). Further, the processing device 120 may determine the termination condition is satisfied if the value of the loss function is less than a threshold. The threshold may be default settings of the medical system 100 or may be adjustable under different situations. As another example, the termination condition may be satisfied if the value of the cost function converges. The convergence may be deemed to have occurred if the variation of the values of the cost function in two or more consecutive iterations is smaller than a threshold (e.g., a constant). As still another example, the processing device 120 may determine the termination condition is satisfied if a specified number (or count) of iterations are performed in the training process. In response to a determination that the termination condition is satisfied, the processing device 120 may designate the machine learning model with the parameter values updated in the last iteration as the trained machine learning model (e.g., the anatomical model). On the other hand, in response to a determination that the termination condition is not satisfied, the processing device 120 may update at least some of the parameter values of the machine learning model based on the assessment result. For example, the processing device 120 may update the value(s) of the learning parameter(s) of the machine learning model based on the value of the loss function according to, for example, a backpropagation algorithm. The processing device 120 may perform the next iteration until the termination condition is satisfied. In the next iteration, the processing device 120 may obtain multiple groups of training samples in another batch. The size of the batch may refer to a group count or number of the multiple groups of training samples. After the termination condition is satisfied in a certain iteration, the machine learning model in the certain iteration having the updated value(s) of the learning parameter(s) may be designated as the trained machine learning model (e.g., the anatomical model).

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 614 and operation 616 may be combined into a single operation. As another example, one or more other optional operations (e.g., a storing operation) may be added elsewhere in the process 600B. In the storing operation, the processing device 120 may store information and/or data (e.g., parameter values, etc.) associated with the training of the machine learning model in a storage device (e.g., the storage device 130) disclosed elsewhere in the present disclosure.

Figure 7:
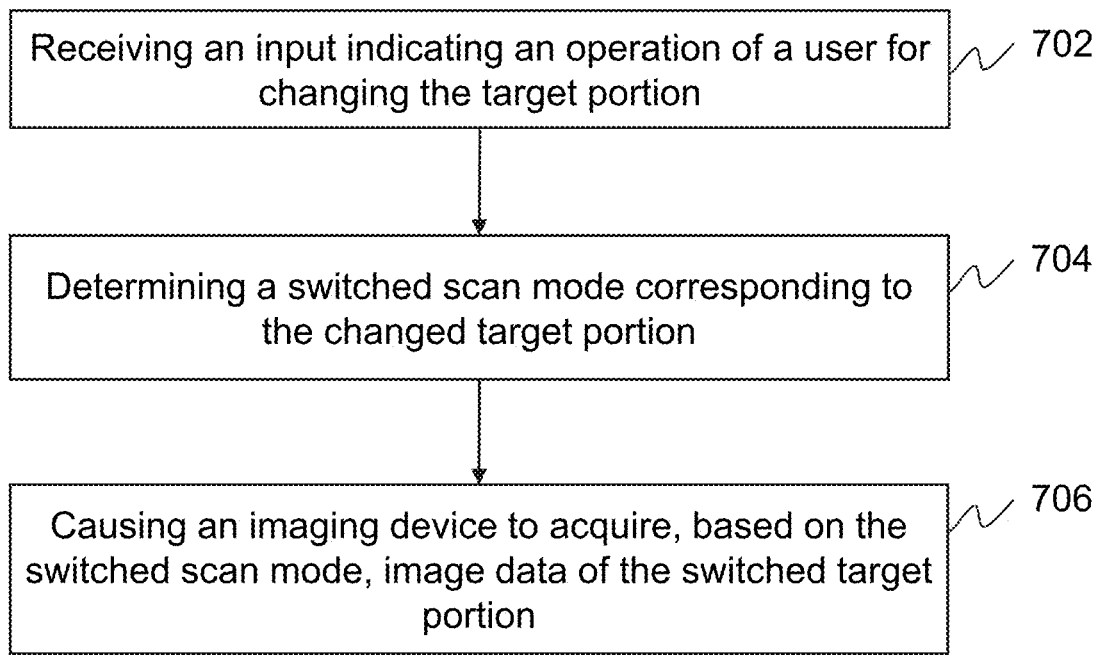
FIG. 7 is a flowchart illustrating an exemplary training process for switching a scan mode according to some embodiments of the present disclosure.

FIG. 7 is a flowchart illustrating an exemplary process for switching a scan mode according to some embodiments of the present disclosure. In some embodiments, process 700 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, the training process of the trained machine learning model as described in connection with operation 508 in FIG. 5 may be performed according to process 700. For illustration purposes, a current iteration of the iteration(s) is described in the following description.

In 702, the processing device 120 (e.g., the acquisition module 410) may receive an input indicating an operation of a user for changing a target portion.

The target portion may be determined as described in connection with operations 502 and 504 illustrated in FIG. 5. For example, the target portion may include the first type of tissue and/or the second type of tissue in the subject. As another example, the processing device 120 may determine an anomaly result indicating whether an anomaly exists in the first type of tissue and/or the second type of tissue. The processing device 120 may determine the target portion according to the anomaly result.

As used herein, the change of the target portion refers to the change in the type of tissue. For example, if the target portion includes the first type of tissue, the changed target portion may include the second type of tissue. In some embodiments, the change of the target portion may be performed before the scanning of the target portion is operated. In some embodiments, the change of the target portion may be performed after the scanning of the target portion is operated.

For example, the user may operate for changing the current target portion when, for example, the current target portion determined by the processing device 120 is not suitable for the subject. The user operation may be achieved via a user interface implemented on a terminal device (e.g., the terminal(s) 140). For example, the user may select or describe the changed target portion on the scout image of the subject via the user interface. The terminal device may generate the input according to the user's operation and transmit the input to the processing device 120. The processing device 120 may receive the input and determine the changed target portion of the subject.

In some embodiments, the input indicating the operation for changing the target portion may include the changed target portion. For example, the user may directly input the changed target portion via the user interface or describe the changed target portion on the scout image of the subject via the user interface. As another example, if the target portion of the subject includes the first type of tissue and the second type of tissue of the subject, the user may select one of the first type of tissue and the second type of tissue as the changed target portion.

In some embodiments, the processing device 120 may determine the changed target portion of the subject according to the target portion. For example, if the current target portion of the subject includes the second type of tissue of the subject, the processing device 120 may determine the changed target portion including the first type of tissue. As another example, if the target portion includes the first type of tissue, the processing device 120 may determine the changed target portion including the second type of tissue. As still another example, if the target portion of the subject includes the first type of tissue and the second type of tissue of the subject, the processing device 120 may designate one of the first type of tissue and the second type of tissue as the changed target portion according to a default setting of the medical system 100 or personalized data of the subject as described elsewhere in the present disclosure (e.g., FIG. 5 and the descriptions thereof).

In 704, the processing device 120 (e.g., the scan mode determination module 430) may determine a switched scan mode corresponding to the changed target portion.

The processing device 120 may update a scan mode corresponding to the target portion according to the changed target portion. The scan mode corresponding to the target portion may be determined as described in connection with operation 506 as described in FIG. 5. In some embodiments, in response to determining the changed target portion, the processing device 120 may determine the switched scan mode corresponding to the changed target portion. For example, if the changed target portion includes the first type of tissue, the processing device 120 may determine the first scan mode (i.e., parallel scan with a plurality of groups of slices oriented at a single angle) as the switched scan mode. As another example, if the changed target portion includes the second type of tissue, the processing device 120 may determine the second scan mode (i.e., an interleaved scan with a plurality of groups of slices oriented at different angles) as the switched scan mode. The processing device 120 may further determine one or more parameters of the switched scan mode according to the changed target portion. The determination of the one or more parameters of the switched scan mode may be similar or the same as the determination of the one or more parameters of the scan mode corresponding to the target portion. More descriptions for determining the one or more parameters of a scan mode may be found elsewhere in the present disclosure (e.g., FIG. 5 and the descriptions thereof).

In 706, the processing device 120 (e.g., the control module 440) may cause an imaging device to acquire image data of the changed target portion based on the switched scan mode. More descriptions regarding the scanning may be found in FIG. 5 and the descriptions thereof.

In some embodiments, the processing device 120 may transmit the acquired image data (e.g., an MR image) to the terminal device. The processing device 120 may further cause the acquired image data to be displayed on the user interface of the terminal device. In some embodiments, the acquired image data may include the image data of the target portion and/or the changed target portion. For example, the user interface of the terminal device may simultaneously display MR images of the target portion and the changed target portion obtained according to the switched scan mode.

In some embodiments, the user interface may include a main view and a secondary view. The main view may include a size (e.g., an area of the main view) exceeding the size of the secondary view. In some embodiments, the main view may be used to display a real-time image and the secondary view may be used to display a historical image. For example, when the target portion is scanned according to the scan mode, the image data of the target portion may be displayed on the main view. When the target portion is changed and the changed target portion is scanned according to the switched scan mode, the image data of the changed target portion may be displayed on the main view and the image data of the target portion may be displayed on the secondary view.

In some embodiments, contents (e.g., the image data) displayed on the two views may be switched. For example, the image data of the target portion displayed on the secondary view may be displayed on the main view, and the image data of the changed target portion displayed on the main view may be displayed on the secondary view. In some embodiments, the processing device 120 may switch the contents displayed on the main and secondary views in response to receiving a user input. For example, when the main view displays the real-time image and the secondary view displays the historical image, the user may click on the secondary view, so that the historical image may be displayed in the main view. When the main view displays the historical image and the secondary view displays the real-time image, the user may click on the secondary view, so that the real-time image may be displayed in the main view.

In some embodiments, the contents displayed in the main view and the secondary view may be updated in real-time. If a subsequent image is reconstructed, the subsequent image may be displayed in the secondary view. When the user clicks the secondary view, the display contents of the main view and the secondary view may be exchanged, so that the real-time image may be viewed in the main view. After the real-time image is viewed, the real-time image of the current view may be moved to the secondary view and saved as a historical image.

Accordingly, the real-time image and historical image may be displayed simultaneously, such that the user may simultaneously observe the real-time image and the historical image. The contents displayed in the main view and the secondary view may be exchanged, such that the user may view the real-time image and historical image according to user preference. The user may observe the image quality in time, determine whether the obtained image is satisfactory, or whether a scanning protocol needs to be changed or continue to be used for scan. More descriptions regarding the scanning protocol may be found elsewhere in the present disclosure (e.g., FIGS. 12A-15B, and the descriptions thereof).

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added elsewhere in the process 700. In the storing operation, the processing device 120 may store information and/or data (e.g., the switched mode, the switched target portion, etc.) associated with the medical system 100 in a storage device (e.g., the storage device 130) disclosed elsewhere in the present disclosure.

Figure 8:
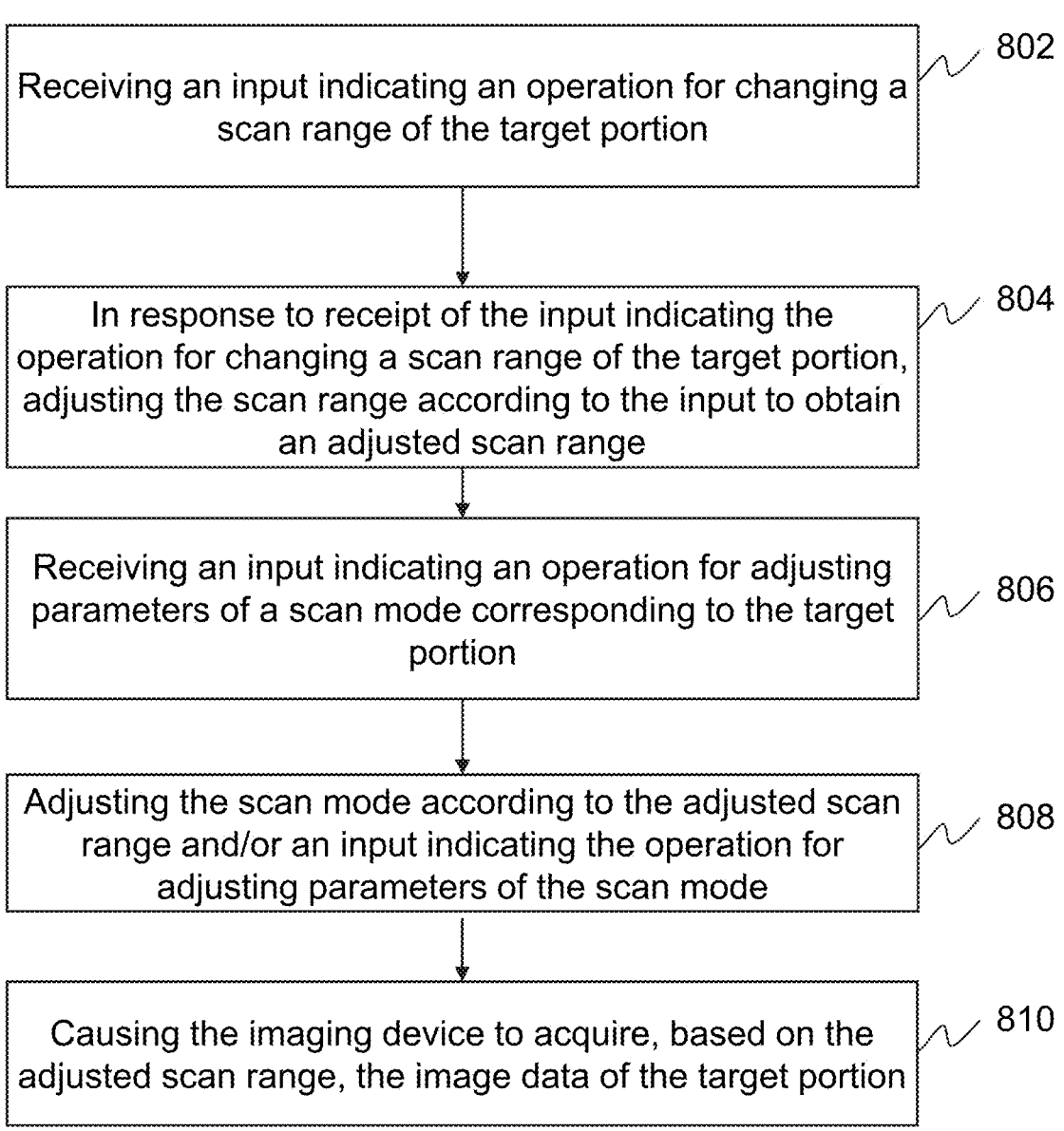
FIG. 8 is a flowchart illustrating an exemplary process for changing a scan mode according to some embodiments of the present disclosure.

FIG. 8 is a flowchart illustrating an exemplary process for adjusting a scan mode according to some embodiments of the present disclosure. In some embodiments, process 800 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, one or more operations of the process 800 may be performed to achieve at least part of operation 506 as described in connection with FIG. 5.

In 802, the processing device 120 (e.g., the acquisition module 410) may receive an input indicating an operation for changing a scan range of a target portion. The target portion may be determined as described in connection with operations 502 and 504 illustrated in FIG. 5. For example, the target portion may include the first type of tissue and/or the second type of tissue in the subject. As another example, the processing device 120 may determine an anomaly result indicating whether an anomaly exists in the first type of tissue and/or the second type of tissue. The processing device 120 may determine the target portion according to the anomaly result.

In some embodiments, after the processing device 120 determines the target portion and the corresponding scan mode, the user (e.g., a doctor, a technician, etc.) may operate, via a user interface implemented on the terminal device, for changing the scan range of the target portion. In some embodiments, the input indicating the operation for changing the scan range of the target portion may include the changed scan range. For example, the processing device 120 may determine that the anomaly exists in one single vertebra of the spine, and determine that the target portion includes the one single vertebra. The user may add all the vertebrae in the spine or multiple vertebrae (e.g., vertebrae in the cervical vertebra, neighboring vertebrae) to the scan range. As another example, the processing device 120 may determine that the anomaly exists in multiple intervertebral discs, and determine that the target portion includes the multiple intervertebral discs. The user may add all intervertebral discs in the spine to the scan range or delete a portion of the multiple intervertebral discs from the scan range.

In some embodiments, the input indicating the operation for changing the scan range may include the changed target portion. For example, the user may directly input the changed scan range via the user interface or describe the changed scan range on the scout image of the subject via the user interface.

In 804, the processing device 120 (e.g., the target portion determination module 420) may adjust the scan range in response to the received input.

In some embodiments, the processing device 120 may adjust the scan range based on the changed scan range included in the user input. For example, referring to FIG. 10, the target portion includes three intervertebral discs in the neck. The user may add a second intervertebral disc 1001 in the neck into the scan range. The second intervertebral disc 1001 in the neck may be selected through an input device (e.g., a mouse) by the user on the scout image. The user may select the second intervertebral disc 1001 from the scout image of the spine and click or touch an addition option on the user interface implemented on the terminal device through the input device. And then the input indicating the operation for adding the second intervertebral disc 1001 in the neck may be transmitted to the processing device 120. The processing device 120 may adjust the scan range from three intervertebral discs in the neck excluding the second intervertebral disc 1001 to the three intervertebral discs in the neck in addition to the second intervertebral disc 1001 in the neck. As another example, referring to FIG. 10, the target portion includes three intervertebral discs. The user may delete the bottom intervertebral disc in the neck (e.g., the fourth intervertebral disc 1002 in the neck) from the scan range so that the scan range includes two intervertebral discs. The bottom intervertebral disc may be selected through an input device (e.g., the mouse). For example, the user may select the bottom intervertebral disc in the neck (e.g., the fourth intervertebral disc 1002 in the neck) from the scout image of the spine and click or touch a delete option on the user interface implemented on the terminal device through the input device. And then the input indicating the operation for deleting the bottom intervertebral disc may be transmitted to the processing device 120. The processing device 120 may adjust the scan range from the three intervertebral discs in the neck to the two intervertebral discs in the neck (excluding the bottom intervertebral disc in the neck).

In some embodiments, the processing device 120 may adjust the scan range according to a default setting of the medical system 100. For example, if the processing device 120 determines that the anomaly exists in one single vertebra. The scan range may include the one single vertebra. The processing device 120 may add all the vertebrae in the spine or a count of rest vertebrae near the one single vertebra to the scan range. As another example, the processing device 120 may determine that the anomaly exists in multiple intervertebral discs. The scan range may include the multiple intervertebral discs. The processing device 120 may add all the intervertebral discs in the spine to the scan range or delete a portion of the multiple intervertebral discs from the scan range.

In 806, the processing device 120 (e.g., the acquisition module 410) may receive an input indicating an operation for adjusting parameters of a scan mode corresponding to the target portion. The scan mode corresponding to the target portion may be determined as described in connection with operation 506 illustrated in FIG. 5.

In some embodiments, after a determination of the target portion and the corresponding scan mode, the user (e.g., a doctor, a technician, etc.) may adjust the parameters (e.g., one or more scan angles, a count of scan slices corresponding to each of the one or more scan angles, a position of each of the scan slices, etc.) of the scan mode corresponding to the target portion.

In some embodiments, after the scan range is adjusted, the user (e.g., a doctor, a technician, etc.) may adjust the parameters (e.g., one or more scan angles, a count of scan slices corresponding to each of the one or more scan angles, a position of each of the scan slices, etc.) of the scan mode corresponding to the adjusted scan range.

In some embodiments, the input indicating the operation for adjusting parameters of the scan mode corresponding to the target portion may include the adjusted values of the parameters of the scan mode. In some embodiments, the user may select one or more parameters to be adjusted and input modified values of the one or more parameters through the input device. For example, the user may directly input a modified count of the scan slices corresponding to a scan angle. In some embodiments, the user may adjust the one or more parameters on the scout image of the subject. For example, the user may add a scan slice, delete a scan slice, adjust the position of a scan slice, adjust the scan angle corresponding to a scan slice, etc., on the scout image through the input device. In some embodiments, the processing device 120 may adjust the value(s) of one or more parameters of the scan mode based on the adjustment made by the user. For instance, in response to an adjusted scan range according to a user input, the processing device 120 may accordingly adjust the position(s), the scan angle(s), etc., of one or more of the scan slices within the adjusted scan range.

In 808, the processing device 120 (e.g., the scan mode determination module 430) may adjust the scan mode according to the adjusted scan range and/or an input indicating the operation for adjusting parameters of the scan mode.

In some embodiments, the adjusting the scan mode may include adjusting the parameters of the scan mode. In some embodiments, the processing device 120 may adjust the parameters according to the adjusted scan mode and/or the adjusted scan range. For example, if the scan range changes from one single vertebra to all the vertebrae in the spine, the count of scan slices may be adjusted according to all the vertebrae in the spine. As another example, if the scan range changes from multiple intervertebral discs in the spine to all the intervertebral discs in the spine, multiple scan angles may be added and a count of scan slices corresponding to each of the added multiple scan angles may be added.

In some embodiments, the processing device 120 may adjust the parameters according to the user input. For example, the target portion may include a second type of tissue (e.g., intervertebral discs), and the corresponding scan mode includes three scan angles and three scan slices corresponding to each of the three scan angles. The input indicating the operation for adjusting parameters of the scan mode may include the adjusted count of scan angles and the adjusted count of each of the scan angles. The processing device 120 may receive the input indicating the operation for adjusting parameters of the scan mode and adjust the scan mode including five angles and two slices corresponding to each of the five scan angles. In some embodiments, the user may delete a few scan slices corresponding to one of the multiple scan angles. The count of scan slices corresponding to the scan angle may be selected through an input device (e.g., the mouse). For example, the user may select the scan slices corresponding to the scan angle and click or touch, through the input device, a delete option on the user interface implemented on the terminal device. And then the input indicating the operation for deleting the scan slices corresponding to the scan angle may be transmitted the processing device 120. The processing device 120 may delete the count of scan slices corresponding to the scan angle to obtain the adjusted scan mode.

In 810, the processing device 120 (e.g., the control module 440) may cause an imaging device to acquire the image data of the target portion based on the adjusted scan range and the adjusted scan mode. More descriptions regarding the scanning may be found in FIG. 5 and the descriptions thereof.

In some embodiments, the adjustment of the scan range may cause a change in the imaging field of view (FOV). Therefore, the count of scan protocols corresponding to the scan range may be adjusted accordingly corresponding to the change of FOV. More descriptions for adjusting the scan protocols may be found in FIGS. 12A-12C, and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added elsewhere in the process 800. In the storing operation, the processing device 120 may store information and/or data (e.g., the adjusted scan range, the input indicating an operation for changing the scan range of the target portion, the adjusted parameter, the input indicating an operation for adjusting parameters of the scan mode, etc.) associated with the medical system 100 in a storage device (e.g., the storage device 130) disclosed elsewhere in the present disclosure.

Figure 11:
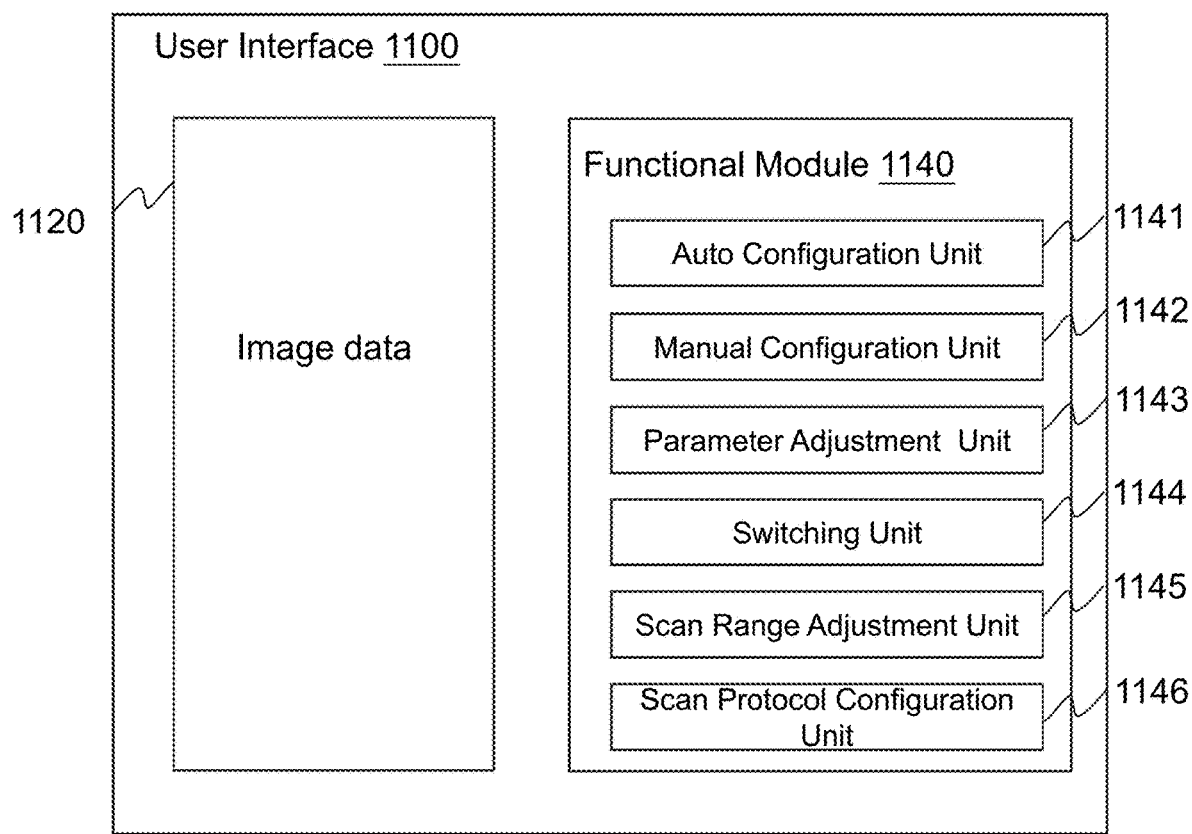
FIG. 11 is a block diagram illustrating an exemplary user interface of a terminal device according to some embodiments of the present disclosure.

FIG. 11 is a block diagram illustrating an exemplary user interface according to some embodiments of the present disclosure. The user interface may be implemented on a terminal device. The terminal device (e.g., the terminal(s) 140) may be connected to and/or communicate with the medical device 110, the processing device 120, and/or the storage device 130. In some embodiments, the terminal device may include a mobile device, a tablet computer, a laptop computer, or the like, or a combination thereof. For example, the mobile device may include a mobile phone, a personal digital assistant (PDA), a gaming device, a navigation device, a point of sale (POS) device, a laptop, a tablet computer, a desktop, or the like, or a combination thereof. In some embodiments, the terminal device may include an input device, an output device (e.g., the display screen 320 as illustrated in FIG. 3), etc., as described elsewhere in the present disclosure (e.g., FIG. 1 and the descriptions thereof). In some embodiments, the terminal device may be part of the processing device 120.

The user interface may be implemented on the terminal device as an application. The user interface may facilitate communication between a user and one or more components in the medical system 100. For example, the terminal device may acquire an input of the user indicating an operation for switching a scan mode via the user interface and transmit the input of the user indicating the operation to the processing device 120. As another example, the processing device 120 may reconstruct one or more images and transmit the one or more images to the terminal device. The one or more images may be displayed for the user via the user interface.

As illustrated in FIG. 11, the user interface 1100 may provide representations of one or more modules implemented on the terminal device and/or on the processing device 120, such as an image data display module 1120, a function module 1140, etc. The function module 1140 may include an auto configuration unit 1141, a manual configuration unit 1142, a parameter adjustment unit 1143, a switching unit 1144, a scan range adjustment unit 1145, and a scan protocol configuration unit 1146. Each of the modules and/or units described above may be implemented by a hardware circuit (e.g., the processing device 120, the CPU 340, etc.) that is designed to perform certain actions, e.g., according to a set of instructions stored in one or more storage media, and/or any combination of the hardware circuit and the one or more storage media. A module or unit may be presented on the user interface as an icon, text, a button, etc. In some embodiments, when the user selects a module or unit via the user interface, the module or unit may perform corresponding actions, e.g., according to a set of instructions stored in one or more storage media. For example, when the user clicks or touches the icon representing the image data display module 1120, the image data display module 1120 may provide one or more views for displaying one or more images.

The image data display module 1120 may be configured to display image data. In some embodiments, the image data display module 1120 may provide one or more views for displaying one or more images. The one or more views may simultaneously display multiple magnetic resonance (MR) images (e.g., the historical image and the real-time image as described in FIG. 7), respectively. In some embodiments, when a user clicks or touches the icon, text, the button, etc., representing the image data display module 1120, the user interface may provide the one or more views. In some embodiments, the user interface may also provide a popup, a dialog, or a new view for the user to select or retrieve the image data to be displayed. More descriptions regarding the image data display may be found in FIG. 7 and the descriptions thereof.

The function module 1140 may provide one or more configuration units for selection as described above. In some embodiments, when a user clicks or touches the icon, text, the button, etc., representing the function module 1140, the user interface may provide the auto configuration unit 1141, the manual configuration unit 1142, the parameter adjustment unit 1143, the switching unit 1144, the scan range adjustment unit 1145, and the scan protocol configuration unit 1146 as shown in FIG. 11 to the user for selection.

The auto configuration unit 1141 may provide a selection that a scan mode for scanning is determined automatically. For example, after the auto configuration unit 1141 is selected by a user, the terminal device may generate an input indicating an operation for selecting the auto configuration unit 1141. The input may be transmitted to the processing device 120. The processing device 120 may determine a scan mode for scanning automatically according to process 500 as described in FIG. 5. For example, the processing device 120 may acquire a scout image of a subject and determine a target portion of the subject that includes an anomaly using an anatomical model. The processing device 120 may further match a scan mode for the target portion. In some embodiments, the user may click or touch the icon, text, the button, etc., that represents the auto configuration unit 1141 to select the auto configuration unit 1141.

The manual configuration unit 1142 may provide a selection that a scan mode for a scanning is determined manually. The user may determine the target portion and the scan mode of the target portion using the manual configuration unit 1142. In some embodiments, after the manual configuration unit 1142 is selected by a user, the user may manually determine the target portion including at least a portion of at least one of the first type of tissue or the second type of tissue via the manual configuration unit 1142. For example, the user may input the target portion via a popup, a dialog, or a new view provided by the manual configuration unit 1142 in response to the selection of the manual configuration unit 1142. As another example, the user may describe the target portion in the scout image displayed via the image data display module 1120 in response to the selection of the manual configuration unit 1142. As still another example, the manual configuration unit 1142 may provide different types of tissue in the subject for selection in response to the selection of the manual configuration unit 1142. The user may select one or more of the different types of tissue in the subject as the target portion.

In some embodiments, the user may determine the corresponding scan mode of the target portion. For example, the user may input the scan mode corresponding to the target portion via a popup, a dialog, or a new view provided by the manual configuration unit 1142 in response to the determination of the target portion. As another example, the manual configuration unit 1142 may provide different types of scan modes (e.g., the first scan mode and the second scan mode as described in FIG. 5) for selection. The user may select one or more of the different types of scan modes.

When the scan mode is determined automatically or manually, the count of scan slices corresponding to each scan angle may be added on the image data (e.g., the scout image) of the subject. For example, if the target portion includes one or more vertebrae, the matching scan mode may be a first scan mode including a parallel scan with a plurality of groups of slices oriented at a single angle. The plurality of groups of slices may be added and distributed at the location on the scout image of the spine corresponding to the one or more vertebrae.

The parameter adjustment unit 1143 may be configured to a selection for adjusting the parameters of the scan mode. The user may adjust one or more parameters of a scan mode via the parameter adjustment unit 1143. In some embodiments, after the parameter adjustment unit 1143 is selected by a user, the user may manually adjust one or more parameters of the scan mode via the parameter adjustment unit 1143. For example, the parameter adjustment unit 1143 may provide a popup, a dialog, or a new view in response to the selection of the parameter adjustment unit 1143. The popup, a dialog, or a new view may provide the parameters of the scan mode. The user may input adjusted values of at least a portion of the parameters of the scan mode directly. As another example, the parameter adjustment unit 1143 may provide multiple reference values of each of the parameters of the scan mode for selection in response to the selection of the parameter adjustment unit 1143. The user may select one from the multiple reference values. As still another example, the user may adjust the one or more parameters on the scout image of the subject. For example, the user may add a scan slice, delete a scan slice, adjust the position of a scan slice, adjust the scan angle corresponding to a scan slice, etc., on the scout image through the parameter adjustment unit 1143.

The switching unit 1144 may be configured to provide a selection for switching the scan mode. In some embodiments, after the switching unit 1144 is selected by a user, the user may manually switch the scan mode. For example, the switching unit 1144 may provide a current scan mode and a switched scan mode in response to the selection of the switching unit 1144. The user may select the switched scan mode. As another example, the switching unit 1144 may provide a current scan mode (e.g., the first scan mode or the second scan mode). In response to the selection of the switching unit 1144, the switching unit 1144 may switch the first scan mode to the second scan mode or switch the second scan mode to the first scan mode.

The scan range adjustment unit 1145 may be configured to provide a selection for adjusting a scan range in response to a received input indicating an operation for changing a scan range of the target portion. The user may adjust the scan range corresponding to the target portion via the scan range adjustment unit 1145. In some embodiments, after the scan range adjustment unit 1145 is selected by a user, the user may manually adjust the scan range of the scan mode via the scan range adjustment unit 1145. For example, the scan range adjustment unit 1145 may provide a popup, a dialog, or a new view in response to the selection of the scan range adjustment unit 1145. The popup, a dialog, or a new view may provide the scan range of the scan mode. The user may input an adjusted scan range (e.g., adding and/or deleting a vertebra and/or an intervertebral disc) of the target portion directly. As another example, the scan range adjustment unit 1145 may provide multiple reference scan ranges of the scan mode for selection in response to the selection of the scan range adjustment unit 1145. The user may select one from the multiple reference scan ranges. As still another example, the user may adjust the scan range (e.g., expand or narrow the scan range) on the scout image of the subject.

The scan protocol configuration unit 1146 may be configured to provide a selection for configuring the scan protocol. The user may configure scan protocols via the scan protocol configuration unit 1146. For example, the scan protocol configuration unit 1146 may provide a popup, a dialog, or a new view in response to the selection of the scan protocol configuration unit 1146. The user may add one or more scan protocols via the popup or the new view popup, a dialog, or a new view. As another example, the user may modify or adjust parameters associated with a scan protocol. More descriptions for configuring the scan protocols may be found in FIGS. 12A-12C, and the descriptions thereof.

It should be noted that the above description is merely provided for illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the auto configuration unit 1141 and the manual configuration unit 1142 may be integrated into a single module. As another example, some other components/modules may be added into the processing device 120.

Figure 12A:
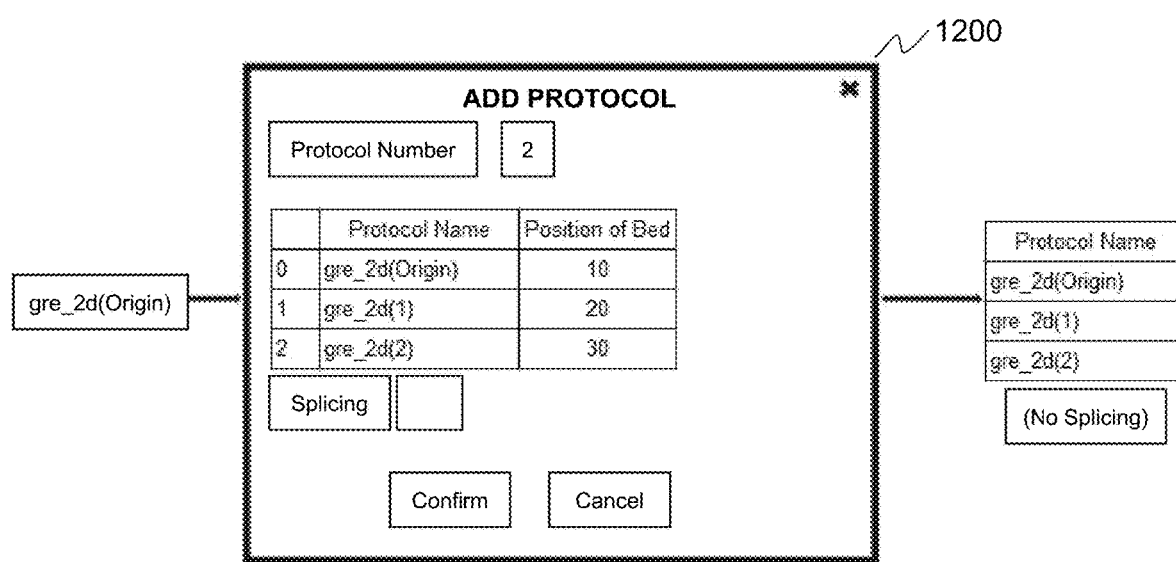
Figure 12B:
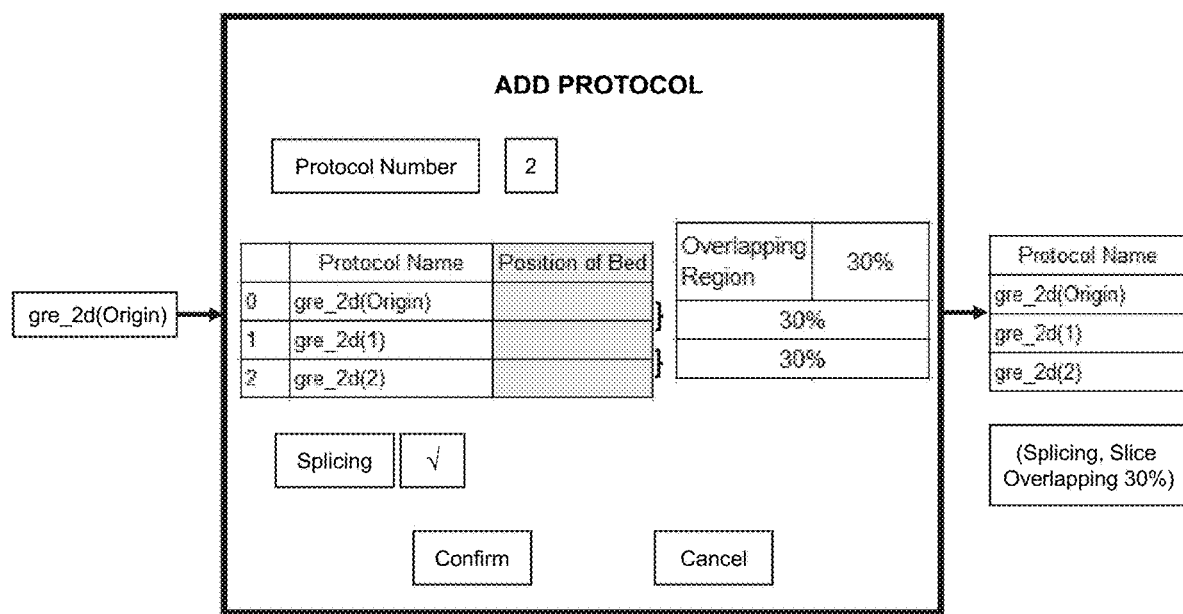
Figure 12C:
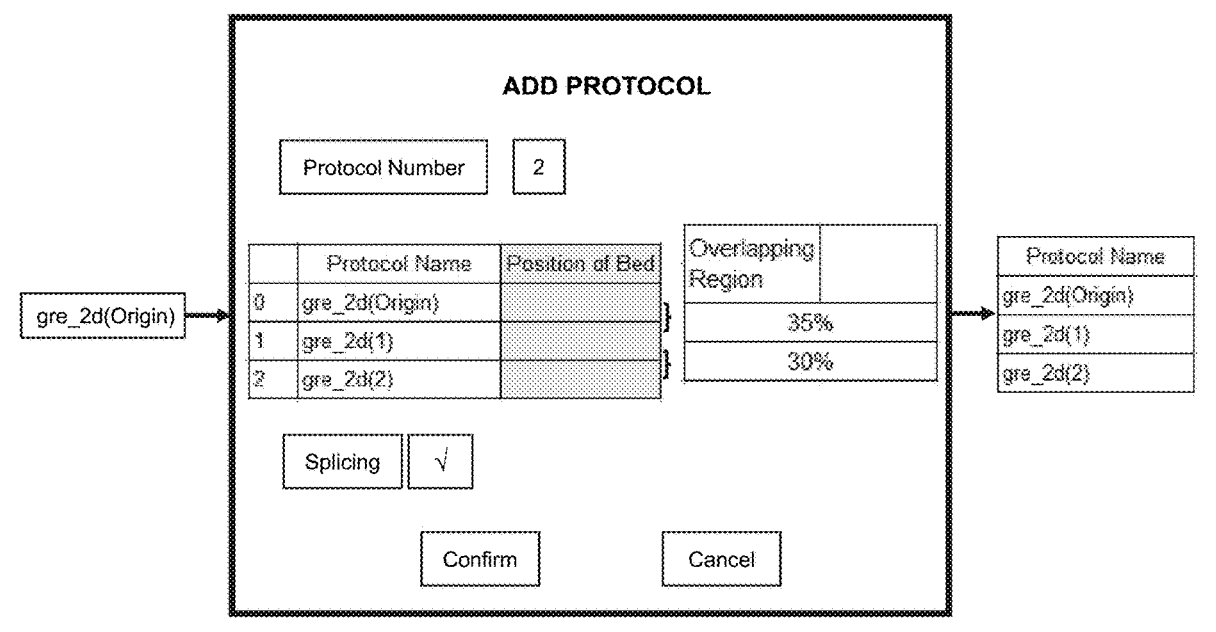

FIGS. 12A-12C are schematic diagrams illustrating an exemplary process for adjusting scan protocols according to some embodiments of the present disclosure.

In some embodiments, a scan range (e.g., a target portion including a second type of tissue) of a target portion may be adjusted or changed as described in FIG. 8. For example, an operator may add more intervertebral discs in the scan range to obtain an adjusted scan range. The scan protocol may be adjusted according to the adjusted scan range. The user may manually adjust the scan protocol via the scan protocol configuration unit 1146 as described in FIG. 11.

As shown in FIG. 12A, an original protocol corresponding to the scan range may be "gre_2d." The user may right click "ADD PROTOCOL." Then, the user interface (e.g., in communication with the scan protocol configuration unit 1146 implemented on a terminal device) may provide a dialog 1200 for adding protocols. A count of added protocols may be inputted by the user or set according to a default setting of the medical system 100. For example, the count of added protocols may be "2." Therefore, two protocols of "gre_2d (1)" and "gre_2d (2)" may automatically be added into a protocol list in the dialog 1200. A position of a bed corresponding to each scan protocol may be edited automatically or manually. The button "Splicing" may be unchecked, and the user may click the button "Confirm." Therefore, the two protocols of "gre_2d (1)" and "gre_2d (2)" may be automatically added in the checklist, and there is no splicing relationship between the two protocols of "gre_2d (1)" and "gre_2d (2)." Different parameters between the two added protocols and the original protocol may be the position of the bed.

In some embodiments, as shown in FIG. 12B, the button "Splicing" may be checked. There may be no need to edit the position of bed corresponding to each scan protocol. "Overlapping Region" between scan slices corresponding to two scan protocols may be adjusted. The "Overlapping Region" between scan slices corresponding to two scan protocols may be set a constant value, such as 30%. After the button "Confirm" is clicked, the two protocols of "gre_2d (1)" and "gre_2d (2)" may be automatically added into the checklist, and there is a splicing relationship among the original protocol and the two protocols. The difference between the two protocols and the original protocol may be the position of the bed. The overlapping region of scan slices corresponding to two scan protocols may be 30% that is determined based on slice images of the subject acquired according to the scan mode and the added scan protocols.

As shown in FIG. 12C, the position of each bed (i.e., reconstruction region) may be set according to scan requirements. The two protocols of "gre_2d (1)" and "gre_2d (2)" may be automatically added into the checklist by the user, and there is a splicing relationship among the original protocol and the two protocols. The difference between the two protocols and the original protocol may be the position of bed. The overlapping region of image slices acquired according to the original protocol and the protocol "gre_2d (1)" may be 35%, and the overlapping region of image slices acquired according to the protocol "gre_2d (1)" and the protocol "gre_2d (2)" may be 30%.

The above embodiments may satisfy the requirement set by the user to manually adjust the scan range of the current target portion. Therefore, the user may have the freedom to increase or decrease the scan range of the current target portion according to the actual requirements.

Figure 13:
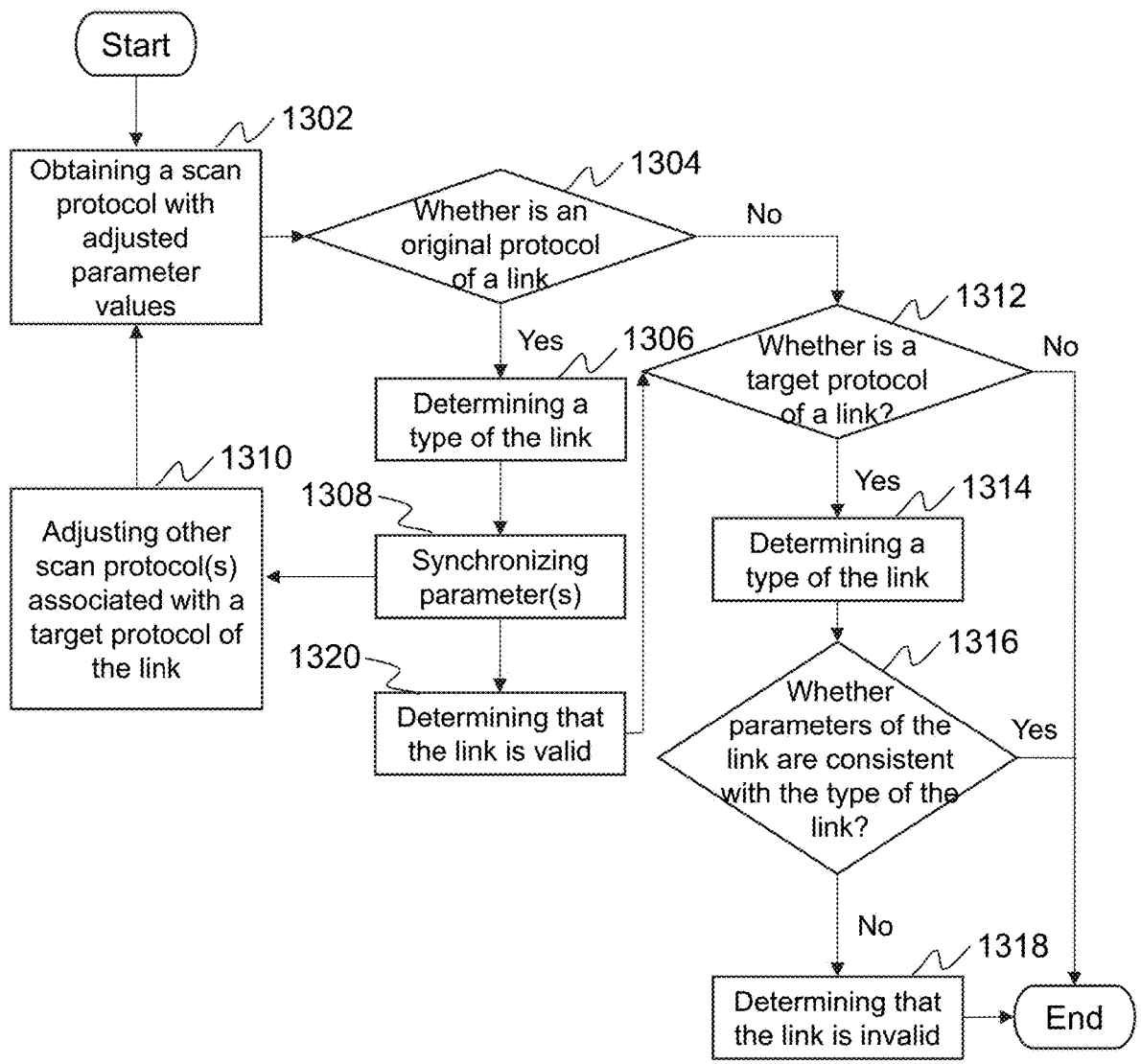
FIG. 13 is a schematic diagram illustrating an exemplary process for synchronizing parameter(s) of scan protocols according to some embodiments of the present disclosure.

FIG. 13 is a schematic diagram illustrating an exemplary process for synchronizing parameter(s) of scan protocols according to some embodiments of the present disclosure. In some embodiments, process 1300 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 500. The operations of the illustrated process presented below are intended to be illustrative. In some embodiments, the process 1300 may be accomplished with one or more additional operations not described and/or without one or more of the operations discussed. Additionally, the order of the operations of the process 1300 illustrated in FIG. 13 and described below is not intended to be limiting.

In some embodiments, a second scan mode may include an interleaved scan with a plurality of groups of slices oriented at different angles. Therefore, the second scan mode may correspond to multiple protocols (or scan protocols). For example, each scan angle may correspond to one of the multiple protocols. In some embodiments, a plurality of parameters of the multiple protocols may be adjusted to be consistent, suitable for a scanning of the target portion. The plurality of parameters corresponding to a scan protocol may include an echo time (TE), an effective TE, an echo train length, an echo space, an inversion time, a number of excitation, an acquisition time, a slice thickness, a slice gap, an FOV, a count of scan slices corresponding to a scan angle, a position and time of a saturation zone, a coil, a position of the bed, etc. If a user manually adjusts the parameters of each scan protocol to keep the parameters consistent between the multiple protocols, it may take a lot of time and be difficult to guarantee the accuracy of the parameters.

Figure 14A:
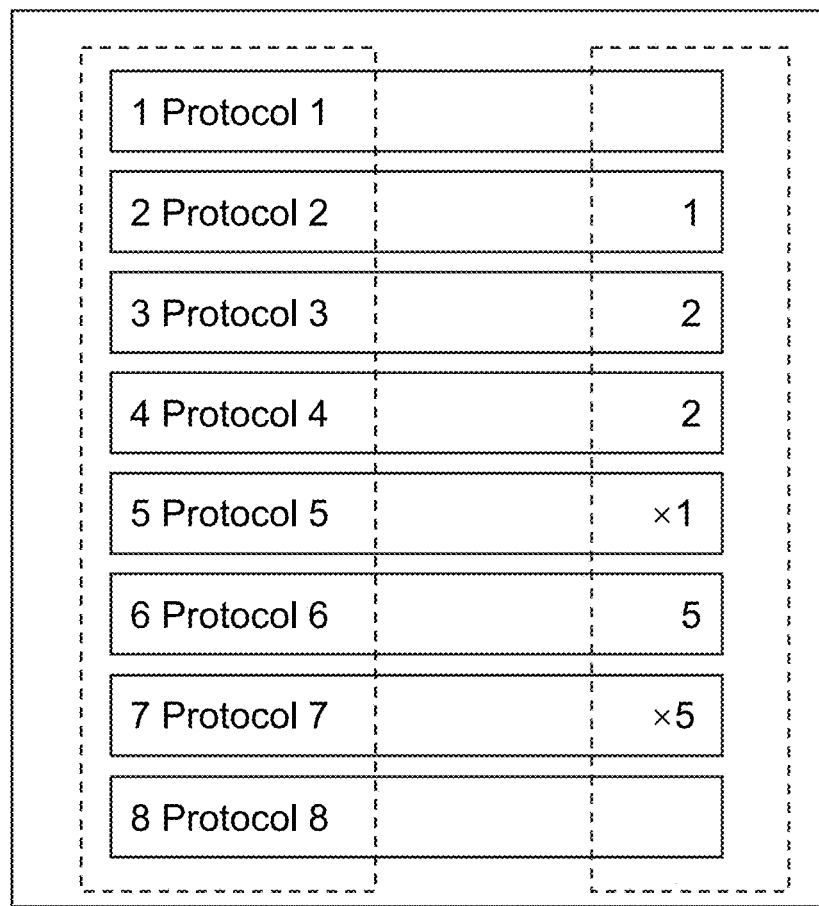

To share or synchronize parameter values between different scan protocols, a link between an original protocol and one or more target protocols may be established. An original protocol of a specific link may include information such as one or more target protocols to which the original protocol links, the types of the link, whether the link is valid, etc. As used herein, an original protocol of a link refers to a scan protocol that has been performed. A target protocol of the original protocol refers to a scan protocol that has not been performed and needs to share some parameters with the original protocol. The original protocol may share parameter values (e.g., an echo time (TE), an effective TE, an echo train length, echo space, an inversion time, a number of excitation, an acquisition time, a slice thickness, etc.) with the two or more target protocols in the link. If the parameter values of a scan protocol of a link are adjusted and the scan protocol has been performed, parameter values of at least one of the two or more target protocols in the link that has not been performed need to be adjusted to consistent with the parameter values of the scan protocol. In some embodiments, a target protocol of the original protocol may be an original protocol in another link. For different links, scan protocols may be different. For example, as shown in FIG. 14A, Protocol 1, Protocol 2, and Protocol 5 may be in a first link. Protocol 1 is an original protocol in the first link, and Protocol 2 and Protocol 5 are target protocols of Protocol 1 in the first link. Protocol 2, Protocol 3, and Protocol 4 may be in a second link. Protocol 2 is an original protocol in the second link, and Protocol 3 and Protocol 4 are target protocols of Protocol 2 in the second link. Protocol 6, Protocol 7, and Protocol 5 may be in a third link. Protocol 5 is an original protocol in the third link, and Protocol 6 and Protocol 7 are target protocols of Protocol 5 in the third link. A type of the link may be defined by names of scan protocols associated with the link that need to share parameters. Whether the link is valid may refer to that whether parameter values of scan protocols in the link are consistent. As shown in FIG. 14A, Protocol 1, Protocol 2, and Protocol 5 may be in the first link. The first link may include a first type defined by names of Protocol 1 and Protocol 2, and a second type defined by names of Protocol 1 and Protocol 5. Parameter values of Protocol 1 and Protocol 5 may be not consistent. The first link Protocol 1, Protocol 2, and Protocol 5 may be invalid.

The information may be saved as a protocol file. Multiple operations, such as read, modification, save, etc., may be performed on the protocol file. The link may include the protocol names of which one or more parameters need to be shared or synchronizes. When a scan protocol is loaded, a determination may be made as to whether the protocol name of the scan protocol exists at the front end of a protocol queue loaded at the same time. If the protocol name of the scan protocol exists at the front end of a protocol queue loaded at the same time, a link between the scan protocol and protocols in the protocol queue may be established. In other words, the scan protocol may be an original protocol of the link and the other protocols in the protocol queue may be target protocols of the link. If the protocol name of the scan protocol does not exist at the front end of a protocol queue loaded at the same time, the link between the scan protocol and protocols in the protocol queue may not be established.

As shown in FIG. 13, in 1302, the processing device 120 may obtain a scan protocol with adjusted parameter values (e.g., Protocol 1 as shown in FIG. 14A). In 1304, the processing device 120 may determine whether the scan protocol is an original protocol of a link. The processing device 120 may determine whether the scan protocol is the original protocol of the link (e.g., the first link between Protocol 1, Protocol 2, and Protocol 5 as shown in FIG. 14A) according to a default setting of the medical system 100. For example, the processing device 120 may determine whether the scan protocol is the original protocol by determining whether the scan protocol has been performed associated with the link. If the scan protocol has been performed, the processing device 120 may determine that the scan protocol is the original protocol of the link. In response to a determination that the scan protocol is the original protocol of the link (e.g., Protocol 1 of the first link as shown in FIG. 14A), the processing device 120 may proceed to perform operation 1306. The processing device 120 may determine a type of the link (e.g., the first type defined by names of Protocol 1 and Protocol 2, and the second type defined by names of Protocol 1 and Protocol 5 as shown in FIG. 14A). In 1308, the processing device 120 may synchronize one or more parameter values of the one or more target protocols (e.g., Protocol 5 as shown in 14A) based on the adjusted parameter values of the scan protocol if the parameters of the scan protocol with the adjusted values belong to shared parameters corresponding to the type of the link (e.g., the second type defined by names of Protocol 1 and Protocol 5 as shown in FIG. 14A). The processing device 120 may determine that the link between the scan protocol (e.g., Protocol 1 as shown in 14B) and the one or more target protocols (e.g., Protocol 2 and Protocol 5 as shown in 14B) is valid in 1320 and proceed to perform operation 1312. In 1310, the processing device 120 may adjust parameter values of other scan protocols (e.g., Protocol 7 as shown in 14B) associated with a target protocol (e.g., Protocol 5 as shown in 14B) of the link. The target protocol (e.g., Protocol 5 as shown in 14B) may be an original protocol of the other scan protocols (e.g., Protocol 7 as shown in 14B) in another a link (the third link between Protocol 6, Protocol 7, and Protocol 5 as shown in 14B). Then the processing device 120 may update the scan protocol obtained in operation 1302 using the target protocol determined in 1310 and repeat process 1300.

In response to a determination that the scan protocol is not the original protocol of the link (e.g., Protocol 2 is not the original protocol of the first link as shown in FIG. 14A), the processing device 120 may proceed to perform operation 1312. In 1312, the processing device 120 may determine whether the scan protocol is a target protocol of the link. In response to a determination that the scan protocol is not a target protocol of the link (e.g., Protocol 3 is the target protocol of the first link as shown in FIG. 14A), the processing device 120 may end process 1300. In response to a determination that the scan protocol is a target protocol of the link (e.g., Protocol 2 is the target protocol of the first link as shown in FIG. 14A), the processing device 120 may proceed to perform operation 1314. In 1314, the processing device 120 may determine the type of the link. In 1316, the processing device 120 may determine whether parameter values of scan protocols associated with the link are consistent. In response to a determination that the parameter values of scan protocols associated with the link are consistent, the processing device 120 may end process 1300. In response to a determination that the parameter values of scan protocols associated with the link are not consistent, the processing device 120 may proceed to perform operation 1318. In 1318, the processing device 120 may determine that the link is invalid and end process 1300.

According to process 1300, when a parameter value of an original protocol associated with a link is changed, the type of link may be determined. If the parameters with changed values belong to the parameters to be shared under the type of link, the changed parameter values may be automatically synchronized throughout the target protocols of the link. If a target protocol is an original protocol of another link and the another link is valid, the above operations may be repeated until the all the scan protocols associated with the scan protocol with adjusted parameter values are synchronized.

Whether a link is valid may be used to indicate whether the parameter values of t the original protocol and the target protocols are consistent under a certain type of link. If a link is valid, no symbol may be displayed on a user interface. If a link is invalid, a special symbol (e.g., "X" as shown in FIG. 14A-14B) may be displayed on a user interface. When the link is invalid, the user may manually confirm an original protocol of the link. Therefore, the synchronization of parameters may be triggered between target protocols and the original protocols, and the link may be shown as valid.

FIGS. 14A-14B are schematic diagrams illustrating an exemplary process for adjusting scan protocols according to some embodiments of the present disclosure.

As shown in FIG. 14A, FIG. 14A shows a display view of a checklist for protocol links. The left dotted block shows protocol numberings and protocol names, such as numbers 1-8 and Protocol 1 to protocol 8, and the right dotted block shows link attributes of the scan protocols each of which indicates whether the scan protocol links to other scan protocol and to which one the scan protocol links. The number located in the right dotted block corresponding to a specific scan protocol represents the numbering of the scan protocol that needs to share parameters with the specific scan protocol. For example, Protocol 3 and Protocol 4 share parameters with Protocol 2. As another example, Protocol 2 shares parameters with Protocol 1. When "X" appears in the front of the number located in the right dotted block corresponding to a specific scan protocol, it may indicate that the parameters between two scan protocols are not consistent. In other words, the link between the two protocols is disconnected. For example, the link between Protocol 5 and Protocol 1 is broken or disconnected. As another example, the link between Protocol 7 and Protocol 5 is broken or disconnected. When a mouse moves over the right dotted block, a hover window may be generated and displayed on the user interface. The hover window may display the type of the link associated with Protocol 1 to protocol 8 and the parameters shared by Protocol 1 to protocol 8 under the type of link. More descriptions regarding the hover window may be found in FIGS. 15A-15B and the descriptions thereof. When the parameter values of Protocol 1 are adjusted, the processing device 120 may synchronize the parameters of all relevant protocols, i.e., Protocol 2 and protocol 5 that are linked to Protocol 1 and reconnect the previously broken links. As shown in FIG. 14B, for example, "X" disappears between Protocol 5 and Protocol 1, i.e., the link between Protocol 5 and Protocol 1 is established. When the parameter values of Protocol 5 are adjusted, the processing device 120 may synchronize the parameters of all protocols, i.e., Protocol 6 and protocol 7 that are linked to Protocol 5.

Figure 15A:
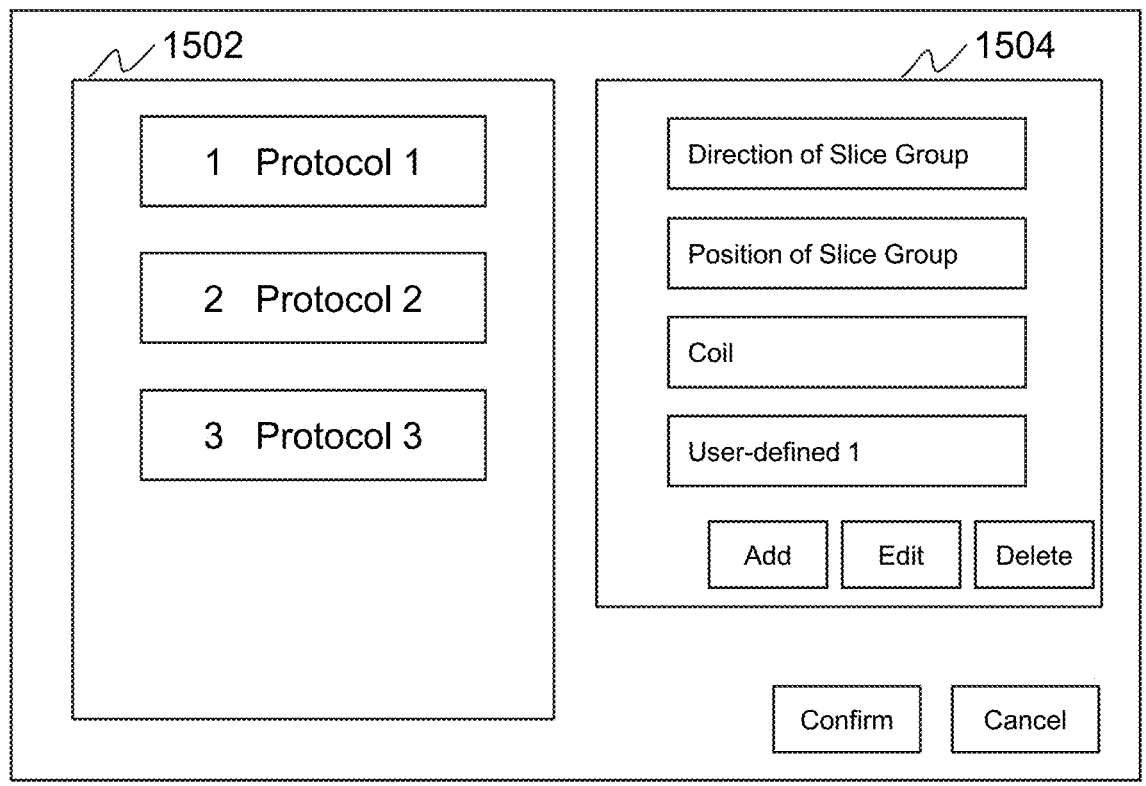

FIGS. 15A-15B are schematic diagrams illustrating an exemplary link setting interface according to some embodiments of the present disclosure.

When a mouse moves over one or more protocols, a hover window of a link setting interface may be generated and displayed. For example, when Protocols 3, 4, and 5 in FIG. 14B is selected, the hover window of the link setting interface shown in FIG. 15A may appear. The left view 1502 shows one or more scan protocols that the selected protocol, Protocols 3, 4, and 5, may be linked to, and the right view 1504 shows optional link types. The link types and the corresponding shared parameters thereof may be adjusted via a protocol file (also referred to as a configuration file). The protocol file may store the numbering of the link, types of the link, parameters (e.g., the numberings of the parameters, parameter values) that are needed to be shared (also referred to as shared parameters) under at least one of the types of the link.

The shared parameters may include a direction of a count of scan slices (i.e., a scan angle corresponding to the count of scan slices as described elsewhere in the present disclosure), a position of a count of scan slices, parameters associated with a coil, or any other user-defined parameters. The coil may include a gradient coil, an RF transmitting coil, and an RF receiving coil. The parameters associated with a coil may include a position where the RF receiving coil is located, a current in an RF transmitting coil, etc. The count of scan slices corresponding to one scan angle may also be referred to as a slice group. Multiple operations, such as addition, modification, deletion, etc., may be performed on the protocol file. When the button "Add" or button "Edit" is selected through an input device (e.g., the mouse), an editing interface of the link types may be displayed as shown in FIG. 15B. Multiple operations, such as editing a name of a link type, modification of a parameter (e.g., the direction of slice group) under the type of the link, etc., may be performed via the editing interface of the link types. The protocol file may be updated based on the operations and the editing interface may be refreshed to display the updated content (e.g., the edited name of the link, the numbering of the link, a modified parameter, e.g., the edited name of the modified parameter, the numbering of the modified parameter) of the protocol file.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python, or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. The latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device storing executable instructions, and
   at least one processor in communication with the at least one storage device, when executing the executable instructions, causing the system to perform operations including:
      obtaining image data of a subject including a first type of tissue and a second type of tissue;
      determining, based on the image data of the subject, a target portion including at least a portion of at least one of the first type of tissue and the second type of tissue;
      determining, based at least in part on the target portion represented in the image data, a scan mode corresponding to the target portion; and causing an imaging device to acquire, based on the scan mode, image data of the target portion, wherein to cause an imaging device to acquire, based on the scan mode, image data of the target portion, the at least one processor is further configured to cause the system to perform the operations including:

receiving an input indicating a change in the target portion;

determining a parallel scan corresponding to the first type of tissue or an interleaved scan corresponding to the second type of tissue as a switched scan mode corresponding to the changed target portion; and causing the imaging device to acquire, based on the switched scan mode, image data of the changed target portion.

2. The system of claim 1, wherein the subject includes a spine, the first type of tissue includes one or more vertebrae, and the second type of tissue includes one or more intervertebral discs.

3. The system of claim 1, wherein to determine, based on the image data of the subject, a target portion including at least a portion of at least one of the first type of tissue and the second type of tissue, the at least one processor is configured to cause the system to perform the operations including:

obtaining an anatomical model; and determining, based on the image data of the subject and the anatomical model, the target portion.

4. The system of claim 1, wherein to determine, based on the image data of the subject, a target portion including at least a portion of at least one of the first type of tissue and the second type of tissue, the at least one processor is configured to cause the system to perform the operations including:

determining, based on the image data of the subject, an anomaly result indicating whether an anomaly exists in at least one of the first type of tissue or the second type of tissue; and determining, based on the anomaly result, the target portion.

5. The system of claim 4, wherein the anomaly result includes that the anomaly exists in the first type of tissue and the second type of tissue; and the determining, based on the anomaly result, the target portion includes determining, based on personalized data of the subject, the target portion including the first type of tissue and the second type of tissue.

6. The system of claim 1, wherein to cause an imaging device to acquire, based on the scan mode, image data of the target portion, the at least one processor is further configured to cause the system to perform the operations:

obtaining multiple scan protocols corresponding to the scan mode; and synchronizing, based on one or more links between the multiple scan protocols, parameter values of at least a portion of the multiple scan protocols.

7. The system of claim 1, wherein to cause an imaging device to acquire, based on the scan mode, image data of the target portion, the at least one processor is further configured to cause the system to perform the operations:

performing a scanning of the target portion according to a first scan mode corresponding to the first type of tissue or a second scan mode corresponding to the first type of tissue;

identifying, based on the scanning, a change of the target portion between the first type of tissue and the second type of tissue; and switching, in response to the identified change, the scan mode between the first scan mode and the second scan mode.

8. The system of claim 1, wherein to determine, based at least in part on the target portion represented in the image data, a scan mode corresponding to the target portion, the at least one processor is further configured to cause the system to perform the operations including:

determining, based at least in part on the target portion, one or more parameters of the scan mode, the one or more parameters of the scan mode including at least one of one or more scan angles, a count of scan slices corresponding to each of the one or more scan angles, or a position of each of the scan slices.

9. The system of claim 1, wherein to cause the imaging device to acquire image data of the target portion, the at least one processor is further configured to cause the system to perform the operations including:

receiving an input indicating an operation for adjusting the scan mode;

in response to the received input, adjusting the scan mode according to the input; and causing an imaging device to acquire, based on the adjusted scan mode, image data of the target portion.

10. The system of claim 1, wherein to cause the imaging device to acquire image data of the target portion, the at least one processor is further configured to cause the system to perform the operations including:

receiving an input indicating an operation for changing a scan range of the target portion;

in response to the received input, adjusting the scan range;

adjusting the scan mode according to the adjusted scan range; and causing the imaging device to acquire, based on the adjusted scan range and the adjusted scan mode, the image data of the target portion.

11. A terminal device including:

at least one storage device storing executable instructions; and at least one processor in communication with a display screen;

when executing the executable instructions, the at least one processor is configured to cause the terminal device to perform operations including:

displaying, on the display screen, a user interface;

detecting, via the user interface, a user input relating to a scan mode; and transmitting, via the user interface, the user input to a processor, wherein the scan mode is provided by a process including:

obtaining image data of a subject including a first type of tissue and a second type of tissue;

determining, based on the image data of the subject, a target portion including at least a portion of at least one of the first type of tissue and the second type of tissue; and determining, based at least in part on the target portion represented in the image data, the scan mode corresponding to the target portion, wherein the user input further indicates an operation for changing the target portion, and the processor is further configured to in response to the received user input, determine a parallel scan corresponding to the first type of tissue or an interleaved scan corresponding to the second type of tissue as a switched scan mode corresponding to the changed target portion;

cause the switched scan mode to be presented on the display screen via the user interface for selection.

12. The terminal device of claim 11, wherein the user input further includes at least one of
   a confirmation of the scan mode,
   a rejection of the scan mode,
   a modification of the scan mode, or
   a selection of another scan mode from the plurality of scan modes.

13. The terminal device of claim 11, wherein the user input further indicates an operation for changing a scan range of the target portion corresponding to the scan mode, and the processor is further configured to:
   in response to the received user input, adjust the scan range;
   adjust the scan mode according to the adjusted scan range; and
   cause the adjusted scan mode to be presented on the display screen via the user interface for confirmation.

14. The terminal device of claim 11, wherein the user input further indicates an operation for adjusting a scan protocol corresponding to the scan mode, and the processor is further configured to:
   in response to the received user input, adjust the scan protocol; and
   cause the adjusted scan protocol to be presented on the display screen via the user interface for confirmation.

15. A method implemented on a computing device including at least one processor and at least one storage device, the method comprising:
   obtaining image data of a subject including a first type of tissue and a second type of tissue;
   determining, based on the image data of the subject, a target portion including at least a portion of at least one of the first type of tissue and the second type of tissue;
   determining, based at least in part on the target portion represented in the image data, a scan mode corresponding to the target portion; and
   causing an imaging device to acquire, based on the scan mode, image data of the target portion, wherein to cause an imaging device to acquire, based on the scan mode, image data of the target portion, the method further including:
   receiving an input indicating a change in the target portion;
   determining a parallel scan corresponding to the first type of tissue or an interleaved scan corresponding to the second type of tissue as a switched scan mode corresponding to the changed target portion; and
   causing the imaging device to acquire, based on the switched scan mode, image data of the changed target portion.

* * * * *